US007341720B2

(12) United States Patent
Stefano

(10) Patent No.: US 7,341,720 B2
(45) Date of Patent: Mar. 11, 2008

(54) TARGETING OF GLYCOPROTEIN THERAPEUTICS

(75) Inventor: James Stefano, Hopkinton, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 11/398,949

(22) Filed: Apr. 5, 2006

(65) Prior Publication Data

US 2006/0228348 A1 Oct. 12, 2006

Related U.S. Application Data

(60) Provisional application No. 60/668,920, filed on Apr. 6, 2005.

(51) Int. Cl.

| | |
|---|---|
| ***A61K 38/54*** | (2006.01) |
| ***A61K 38/43*** | (2006.01) |
| ***A61K 38/16*** | (2006.01) |
| ***C12N 9/40*** | (2006.01) |
| ***C07K 16/00*** | (2006.01) |

(52) U.S. Cl. ........................ 424/94.3; 424/94.1; 514/8; 435/208; 435/188.5

(58) Field of Classification Search ..................... None
See application file for complete search history.

(56) References Cited

U.S. PATENT DOCUMENTS

| | | | |
|---|---|---|---|
| 4,701,521 A | 10/1987 | Ryser et al. | |
| 4,749,570 A | 6/1988 | Poznansky | |
| 5,206,370 A | 4/1993 | Schwartz et al. | |
| 5,420,285 A | 5/1995 | Schwartz et al. | |
| 5,521,290 A | 5/1996 | Sivam et al. | |
| 5,753,520 A | 5/1998 | Schwartz et al. | |
| 5,769,778 A | 6/1998 | Abrams et al. | |
| 5,863,990 A | 1/1999 | Papisov | |
| 6,399,575 B1 | 6/2002 | Smith et al. | |
| 6,562,316 B1 | 5/2003 | Edwards et al. | |
| 6,569,451 B1 | 5/2003 | Li et al. | |
| 6,676,963 B1 | 1/2004 | Lanza et al. | |
| 6,703,488 B1 | 3/2004 | Burton et al. | |
| 6,749,865 B2 | 6/2004 | Calias et al. | |
| 6,800,273 B2 | 10/2004 | Rajopadhye et al. | |
| 2002/0137125 A1 | 9/2002 | Zhu | |
| 2003/0082176 A1 | 5/2003 | LeBowitz et al. | |
| 2004/0132640 A1* | 7/2004 | DeFrees et al. | 514/8 |
| 2005/0169968 A1 | 8/2005 | Elmaleh et al. | |
| 2005/0281805 A1 | 12/2005 | LeBowitz et al. | |
| 2006/0051317 A1 | 3/2006 | Batrakova et al. | |

FOREIGN PATENT DOCUMENTS

| | | |
|---|---|---|
| EP | 384 769 | 8/1990 |
| WO | WO 92/16555 | 10/1992 |
| WO | WO 01/60412 | 8/2001 |
| WO | WO 01/60412 A2 * | 8/2001 |
| WO | WO 01/90139 | 11/2001 |
| WO | WO 02/07671 | 1/2002 |
| WO | WO 02/057445 | 7/2002 |
| WO | WO 03/005719 A2 * | 7/2003 |
| WO | WO 03/057179 | 7/2003 |
| WO | WO 2005/002515 | 1/2005 |
| WO | WO 2005/077093 | 8/2005 |

OTHER PUBLICATIONS

Gregoriadis et al., Polysialic acids: potential in drug delivery. FEBS, 1993, vol. 315 (3): 271-276.*

Abraham et al., Heparin-Binding EGF-Like Growth Factor: Characterization of Rat and Mouse CDNA Clones, Protein Domain Conservation Across Species, and Transcript Expression in Tissues, *Biochem. Biophys. Res. Commun.*, 190-125-133, 1993.

Casares et al., Antigen-specific downregulation of T cells by doxorubicin delivered through a recombinant MHC II-peptide chimera, *Nature Biotechnol.*, 19:142-147, 2001.

Cavallaro et al., Glycosilated Macromolecular Conjugates of Antiviral Drugs with a Polyaspartamide, *J. Drug Targeting*, 12:593-605, 2004.

Day et al., Induction of Antigen-Specific CTL Responses Using Antigens Conjugated to Short Peptide Vectors, *J. Immunol.*, 170:1498-1503, 2003.

Demeule et al., High Transcytosis of melanotransferrin (P97) across the blood-brain barrier, *J. Neurochem.*, 83:924-933, 2002.

Derossi et al., Trojan peptides: the penetratin system for intracellular delivery, *Trends Cell Biol.*, 8:84-87, 1998.

Dubowchik et al., Cathespin B-Labile Dipeptide Linkers for Lysosomal Release of Doxorubicin from Internalizing Immunoconjugates: Model Studies of Enzymatic Drug Release and Antigen-Specific In Vitro Anticancer Activity, *Bioconjugate Chem.*, 13:855-869, 2002.

(Continued)

*Primary Examiner*—Rebecca E. Prouty
*Assistant Examiner*—Ganapathirama Raghu
(74) *Attorney, Agent, or Firm*—Finnegan, Henderson, Farabow, Garrett & Dunner, L.L.P.

(57) ABSTRACT

Methods of making ligand-decorated polymer conjugates of therapeutic glycoproteins are described. Improved targeting of glycoproteins to specific tissues is achieved by masking the natural carbohydrate and other surface determinants with high molecular weight polymers, such as, e.g., PEG, polysialic acid, etc., which in turn are decorated with target-specific ligands. In some embodiments, acid-labile linkages in such conjugates or rapidly degradable masking groups allow for the intracellular release of the polymer from the glycoprotein, for example, under conditions found in lysosomes.

18 Claims, 10 Drawing Sheets

OTHER PUBLICATIONS

Duncan et al., A New Reagent Which May Be Used to Introduce Sulfhydryl Groups into Proteins, and Its Use in the Preparation of Conjugates for Immunoassay, *Anal. Biochem.*, 132:68-73, 1983.

Elliott et al., Intercellular Trafficking and Protein Delivery by a Herpesvirus Structural Protein, *Cell*, 88:223-233, 1997.

Etrych et al., New HPMA copolymers containing doxorubicin bound via pH-sensitive linkage: synthesis and preliminary in vitro and in vivo biological properties, *J. Controlled Release*, 73:89-102, 2001.

Fawell et al., Tat mediated delivery of heterologous proteins into cells, *Proc. Natl. Acad. Sci. U.S.A.*, 91:664-668, 1994.

Freireich et al., Quantitative Comparison of Toxicity of Anticancer Agents in Mouse, Rat, Hamsetr, Dog, Monkey, and Man, *Cancer Chemother. Rep.*, 50:219-244, 1966.

Friden et al., Characterization, Receptor Mapping and Blood-Brain Barrier Transcytosis of Antibodies to the Human Transferrin Receptor, *J. Pharmacol. Exp. Ther.*, 278:1491-1498, 1996.

Funhoff et al., PEG shielded polymeric double-layered micelles for gene delivery, *J. Controlled Release*, 102:711-724, 2005.

Furbish et al., Uptake and distribution of placental glucocerebrosidase in rat hepatic cells and effects of sequential deglycosylation, *Biochim. Biophys. Acta*, 673:425-434, 1981.

Gaillard et al., Targeted delivery across the blood-brain barrier, *Expert Opin. Drug Deliv.*, 2:299-309, 2005.

Geoghegan et al., Site-Directed Conjugation of Nonpeptide Groups to Peptides and Proteins via Periodate Oxidation of a 2-Amino Alcohol. Application to Modification at N-Terminal Serine, *Bioconjugate Chem.*, 3:138-146, 1992.

Hamann et al., An Anti-CD33 Antibody-Calicheamicin Conjugate for Treatment of Acute Myeloid Leukemia. Choice of Linker, *Bioconjugate Chem.*, 13:40-46, 2002.

Hembrough et al., Identification and characterization of a very low density lipoprotein receptor-binding peptide from tissue factor pathway inhibitor that has antitumor and antiangiogenic activity, *Blood*, 103:3374-3380, 2004.

Hinman et al., Preparation and Characterization of Monoclonal Antibody Conjugates of the Calicheamicins: A Novel and Potent Family of Antitumor Antibiotics, *Cancer Res.*, 53:3336-3342, 1993.

Horinouchi et al., Acid sphingomyelinase deficient mice: a model of types A and B Niemann-Pick disease, *Nat. Genet.*, 10:288-293, 1995.

Jeyakumar et al., Glycosphingolipid lysosomal storage diseases: therapy and pathogenesis, *Neuropath. Appl. Neurobiol.*, 28:343-357, 2002.

Kamada et al., Synthesis of a poly(vinylpyrrolidone-co-dimethyl maleic anhydride) co-polymer and its application for renal drug targeting, *Nat. Biotechnol.*, 21:399-404, 2003.

Kaneko et al., New Hydrazone Derivatives of Adriamycin and Their Immunoconjugates-a Correlation between Acid Stability and Cytotoxicity, *Bioconjugate Chem.*, 2:133-141, 1991.

King et al., Monoclonal Antibody Conjugates of Doxorubicin Prepared with Branched Linkers: A Novel Method for Increasing the Potency of Doxorubicin Immunoconjugates, *Bioconjugate Chem.*, 10:279-288, 1999.

Kolonin et al., Reversal of obesity by targeted ablation of adipose tissue, *Nature Med.*, 10:625-632, 2004.

Lanciotti et al., Targeting Adenoviral Vectors Using Heterofunctional Polyethylene Glycol FGF2 Conjugates, *Mol. Ther.*, 8:99-107, 2003.

Lebowitz et al., Glycosylation-independent targeting enhances enzyme delivery to lysosomes and decreases storage in mucopolysaccharidosis type VII mice, *Proc. Natl. Acad. Sci. U.S.A.*, 101:3083-3088, 2004.

Lecolley et al., A new approach to bioconjugates for proteins and peptides ("pegylation") using living radical polymerisation, *Chem. Commun.*, 18:2026-2027, 2004.

Lee et al., Receptor mediated uptake of peptides that bind the human transferrin receptor, *Eur. J. Biochem.*, 268:2004-2012, 2001.

Lisi et al., Polyethylene Glycol:β-Glucuronidase Conjugates as Potential Therapeutic Agents in Acid Mucopolysaccharidosis, *J. Appl. Biochem.*, 4:19-33, 1982.

Mann et al., Endocytosis and targeting of exogenous HIV-1 Tat protein, *EMBO J.*, 10:1733-1739, 1991.

Marshall et al., Demonstration of Feasibility of In Vivo Gene Therapy for Gaucher Disease Using a Chemically Induced Mouse Model, *Mol. Ther.*, 6(2):179-189, 2002.

Mayes et al., Differential assay for lysosomal alpha-galactosidases in human tissues and its application to Fabry's disease, *Clin. Chim. Acta.*, 112:247-251, 1981.

Mceachern et al., AAV8-mediated expression of glucocerebrosidase ameliorates the storage pathology in the visceral organs of a mouse model of Gaucher disease, *J. Gene Med.*, 8:719-729, 2006.

Mitchell et al., Polyarginine enters cells more efficiently than other polycationic homopolymers, *J. Peptide Res.*, 56:318-325, 2000.

Mizukami et al., Systemic inflammation in glucocerebrosidase-deficient mice with minimal glucosylceramide storage, *J. Clin. Invest.*, 109:1215-1221, 2002.

Munier-Lehmann et al., Re-expression of the Mannose 6-Phosphate Receptors in Receptor-deficient Fibroblasts, *J. Biol. Chem.*, 271:15166-15174, 1996.

Muranganandam et al., Selection of phage-displayed Ilama single-domain antibodies that transmigrate across human blood-brain barrier endothelium, *FASEB J.*, 16:240-242, 2002.

Ohkuma et al., Fluorescence probe measurement of the intralysosomal pH in living cells and the perturbation of pH various agents, *Proc. Natl. Sci. Acad. U.S.A.*, 75:7:3327-3331, 1978.

Ohshima et al., α-Galactosidase A deficient mice: A model of Fabry disease, *Proc. Natl. Acad. Sci. U.S.A.*, 94:2540-2544, 1997.

Papisov, Acyclic polyacetals from polysaccharides, *ACS Symposium Series*, 786:301-314, 2001.

Papisov et al., Hydrophilic Polyals: Biomimetic Biodegradable Stealth Materials for Pharmacology and Bioengineering Abstract, *226th American Chemical Society National Meeting*. New York, NY, Sep. 7-11, 2003.

Papisov et al., Hydrophilic Polyals: Biomimetic Biodegradable Stealth Materials for Pharmacology and Bioengineering.

Papisov et al., Semisynthetic Hydrophilic Polyals, *Biomacromolecules*, 6:2659-2670, 2005.

Poznansky et al., α-1,4-Glucosidase-albumin polymers: in vitro properties and advantages for enzyme replacement therapy, *Can. J. Physiol. Pharmacol.*, 58:322-325, 1980.

Poznansky et al., Insulin Carrier Potential for Enzyme and Drug Therapy, *Science*, 223:1304-1306, 1984.

Prince et al., Lipoprotein Receptor Binding, Cellular Uptake, and Lysosomal Delivery of Fusions between the Receptor-associated Protein (RAP) and α-L-Iduronidase or Acid α-Glucosidase, *J. Biol. Chem.*, 279:35037-35046, 2004.

Raben et al., Targeted Disruption of the Acid α-Glucosidase Gene in Mice Causes an illness with Critical Features of Both Infantile and Adult Human Glycogen Storage Disease Type II, *J. Biol. Chem.*, 273(3):19086-19092, 1998.

Romanczuk et al., Modification of an Adenoviral Vector with Biologically Selected Peptides: A Novel Strategy for Gene Delivery to Cells of Choice, *Hum. Gene Ther.*, 10:2615-2626, 1999.

Roussele et al., New Advances in the Transport of Doxorubicin through the Blood-Brain Barrier by a Peptide vector-Mediated Strategy, *Mol. Pharmacol.*, 57:679-686, 2000.

Schnyder et al., Targeting of Skeletal muscle n vitro using biotinylated immunoliposomes, *Biochem. J.*, 377:61-67, 2004.

Schwarze et al., In Vivo Protein Transduction: Delivery of a Biologically Active Protein into the Mouse, *Science*, 285:1569-1572, 1999.

Shen et al., Conjugation of poly-L-lysine to albumin and horseradish peroxidase: A novel method of enhancing the cellular uptake of proteins, *Proc. Natl. Acad. Sci. U.S.A.*, 75:1872-76, 1978.

Srinivasachar et al., New Protein Cross-Linking Reagents That Are Cleaved by Mild Acid, *Biochemistry*, 28:2501-2509, 1989.

Wang et al., Single-Chain Fv with manifold *N*-glycans as bifunctional scaffolds for immunomolecules, *Protein Eng.*, 11:12:1277-1283, 1998.

Wender et al., The design, sythesis and evaluation of molecules that enable or enhance cellular uptake: Peptoid molecular transporters, *Proc. Natl. Acad. Sci. U.S.A.*, 97:13003-13008, 2000.

Wieder et al., Enzyme Therapy: II. Effect of Covalent Attachment of Polyethylene Glycol on Biochemical Parameters and Immunological Determinants of β-Glucosidase and α-Galacatosidase, *J. Appl. Biochem.*, 5:337-347, 1983.
Yurkovetskiy et al., Fully Degradable Hydrophilic Polyals for Protein Modification, *Biomacromolecules*, 6:2648-2658, 2005.
Zalipsky et al., Hydrazide Derivatives of Poly(ethylene glycol) and Their Bioconjugates, *Poly(ethylene glycol) Chemistry and Biological Applications*, 680:318-341, 1997.
Zara et al., A Carbohydrate-Directed Heterobifunctional Cross-Linking Reagent for the Synthesis of Immunoconjugates, *Anal. Biochem.*, 194:156-162, 1991.
Zhang et al., Global Non-Viral Gene Transfer to the Primate Brain Following Intravenous Administration, *Mol. Ther.*, 7:1-8, 2003.
International Search Report for International Application No. PCT/US2006/012698, dated Nov. 10, 2006, Examiner Ramon N. Gonzalez.
Bowie et al., "Deciphering the Message in Protein Sequences: Tolerance to Amino Acid Substitutions," *Science* 247:1306-1310 (1990).
Branden et al., Introduction to Protein Structure, pp. 358-366 (Garland Publishing, Inc., 2d ed., 1999).
Dvir et al., "X-ray structure of human acid-β-glucosidase, the defective enzyme in Gaucher disease," *EMBO Reports*, 4:1-6 (2003).
Garman et al., "Structural Basis of Fabry Disease," *Mol. Genet. Metabol.*, 77:3-11 (2002).
Garman et al., "The Molecular Defect Leading to Fabry Disease: Structure of Human α-Galactosidase," *J. Mol. Biol.*, 337:319-335 (2004).
Liou et al., "Analyses of Variant Acid β-Glucosidases. Effects of Gaucher Disease Mutations," *J. Biol. Chem.*, 281:4242-4253 (2006).
Matsuzawa et al., Fabry disease: correlation between structural changes in a-galactosidase, and clinical and biochemical phenotypes, *Hum. Genet.* 117:317-328 (2005).
Miller et al., "Genetic Studies of the Iac Repressor. IX. Generation of Altered Proteins by the Suppression of Nonsence Mutations," *J. Mol. Biol.* 131:191-222 (1979).
Minko et al., "Molecular Targeting of Drug Delivery Systems to Cancer," *Current Drug Targets*, 5:389-406 (2004).
Table of Contents, *Adv. Drug Delivery Rev.*, vol. 53, Issue 2 (Dec. 17, 2001).
Table of Contents, *Adv. Drug Delivery Rev.*, vol. 54, Issue 4 (Jun. 17, 2002).
Table of Contents, *Adv. Drug Delivery Rev.*, vol. 55, Issue 2 (Feb. 10, 2003).
Table of Contents, *Adv. Drug Delivery Rev.*, vol. 56, Issue 4 (Mar. 3, 2004).
Table of Contents, *Adv. Drug Delivery Rev.*, vol. 57, Issue 4 (Feb. 28, 2005).
Torchilin, "Drug Targeting," *Eur. J. Pharm. Sci.* 11:S81-S91 (2000).

* cited by examiner

TARGETING OF GLYCOPROTEIN THERAPEUTICS

This application claims priority to U.S. provisional application No. 60/668,920, filed on Apr. 6, 2005, which is incorporated by reference in its entirety.

FIELD OF THE INVENTION

The invention relates to protein therapeutics and, more specifically, to conjugation of such therapeutics with other molecular moieties to achieve tissue-specific targeting in the body, followed by the intracellular release of the biologically active therapeutic at the site of action, as exemplified by replacement lysosomal enzymes conjugated with ligand-decorated polymers and the use of such conjugates for treatment of lysosomal storage disorders.

BACKGROUND OF THE INVENTION

Tissue-specific targeting of therapeutic proteins to tissues of choice in the body finds application in many medical conditions including cancer and a number of acquired and inherited disorders. For example, in the class of diseases called lysosomal storage disorders, an inherited deficiency in one or more enzymes which reside in the lysosomes leads to the accumulation of substrates for those enzymes in the cells. Because of tissue-specific patterns of expression and accumulation of the substrates within different cells in the body, these disorders result in tissue/organ-specific manifestations which vary depending upon the disorder. These disorders have been found to be treatable by intravenous administration of the active version of the enzyme deficient in the patient, a process termed enzyme replacement therapy (ERT). However, the efficacy of ERT varies widely among the different disorders. Although the reasons for this variability are not fully understood, it is commonly believed to be due to the lack of specific targeting to the most seriously affected tissues.

Most lysosomal proteins are glycoproteins containing one or more N- or O-linked oligosaccharide side chains of high mannose, complex or hybrid type. A number of receptors specific for these sugar residues exist, including among others, those for mannose, galactose (asialoglycoprotein receptor, ASGPR) and mannose-6-phosphate (cation-independent mannose-6-phosphate receptor, CIMPR). These receptors at least in part mediate the uptake of administered protein into cells. However, the distribution of these receptors within tissues in the body (e.g., ASGPR expressed on liver hepatocytes, mannose receptor on cells of the reticuloendothelial system such as macrophages and Kupffer cells of the liver and CIMPR expressed widely on endothelial cells as well as other cell types) is not optimal for targeting proteins to the tissues which are most strongly affected. In some cases, modification and/or removal of a portion or all of the oligosaccharide chains through a process termed remodeling can advantageously improve the ultimate biodistribution of the proteins to more specifically target the protein to desired cell types (see, e.g., Furbush et al. Biochimica et Biophysica Acta 673:425-434 (1981), which describes sugar remodeling for a recombinant glucocerebrosidase, imiglucerase (Cerezyme®, Genzyme Corporation, Cambridge, Mass.)). However, complete removal of the carbohydrate side chains is often counterproductive, since they are also often necessary for the solubility and/or intracellular stability of the protein.

Another difficulty encountered with ERT is the strong immunogenicity of some therapeutic proteins as the patient's immune system often recognizes such proteins as foreign and mounts a neutralizing immune response. Thus, a means to reduce the exposure of the therapeutic proteins to the immune system would also be desirable.

Covalent conjugation with polymers such as polyethylene glycol (PEG) generally increases the serum half-life of a number of therapeutics such as antibodies, interferon, and effector molecules, while also reducing their immunogenicity. Although maintaining elevated concentrations of administered lysosomal proteins in circulation would similarly be expected to increase their bioavailability, in the case of lysosomal proteins, conjugation of these proteins with PEG ("PEGylation") alone does not appear to be effective. This may partly be due to the adverse effect of the conditions in plasma, particularly elevated pH, on enzyme stability, and also on the inability of PEG, a neutral hydrophilic polymer, to influence the relative affinity of the glycoproteins for various receptor systems and to introduce any new tissue tropism to the protein. Thus, an additional means to promote uptake into the lysosomes of cells, and specifically the cells in those tissues in which substrate has accumulated in the body, would be highly desirable. In some cases, this can be achieved by the affinity of the polymer itself for specific tissue types (e.g., PVP-DMMan polymer conjugates for targeting a therapeutic to the kidneys are described in Kamada et al., Nat. Biotech. (2003) 21:399-404). Alternatively, it may be achieved by the introduction of ligands into the conjugate to promote interaction with tissue-specific receptors to mediate uptake. In the simplest case, such ligands are represented by antibodies against the receptor of choice. However, the larger proteinaceous ligands, such as antibodies, can themselves be immunogenic, thus posing significant challenges in the clinic.

Additionally, conjugation of a therapeutic protein with high molecular weight polymers may interfere with the activity of the protein at the site of action in the cell. For example, it has been found that many of the lysosomal enzymes, particularly those that act on glycolipid substrates, require a cofactor from the class termed saposins for their enzymatic activity. Saposins are believed to assist in presentation of the carbohydrate head group of the substrate to the catalytic site. Thus, conjugation of a high molecular weight polymer to the enzyme might affect the enzyme's activity by interfering with interactions with saposins, thereby lowering the efficacy of the therapeutic. Accordingly, a means to provide for elimination of the polymer from the enzyme in the site of action would be desirable.

On the other hand, another factor contributing to lowered efficacy of enzyme replacement therapies is the instability of lysosomal proteins within the lysosome, leading to a need for repeated administration. For example, Cerezyme® (glucocerebrosidase) is generally administered to a patient having Gaucher's disease on a biweekly basis due to loss of its activity after being taken up by target cells. The loss of activity is at least in part due to the action of lysosomal proteases on the protein, and appending polymers such as PEG can increase the resistance of proteins to proteolysis. Thus, under certain circumstances, a polymer may serve the additional function of protecting the protein in the lysosomal environment, thereby providing better intralysosomal stability of the active protein. Such a strategy may be effective in reducing the frequency of administration.

Low molecular weight ligands, such as peptides or mono- or oligosaccharides, may be used for targeting a therapeutic protein. However, such ligands often must be present in multiple copies on a macromolecule in order to mediate effective uptake by the cognate receptor, a condition termed "multivalent display." Although current commercially available heterobifunctional PEGs (e.g., linear molecules containing different chemical entities on each terminus) may be used to generate ternary conjugates, they do not provide for multivalent display except by the attachment of multiple PEG molecules. But such heavy modification often has an adverse effect on enzyme activity.

Therefore, there exists a continuing need to provide protein therapeutics that allow for target-specific delivery within the body and are sufficiently biologically active upon intracellular uptake.

SUMMARY OF THE INVENTION

The present invention provides ternary conjugates of a therapeutic glycoprotein, a masking moiety, and a targeting moiety. A conjugate of the invention includes:

(1) a therapeutic glycoprotein (G), (2) a masking moiety (M) covalently linked to an oligosaccharide side chain of the glycoprotein through a first linker ($L^1$), and (3) a targeting moiety (T) covalently linked to the masking moiety through a second linker ($L^2$), wherein the glycoprotein is released from the conjugate under lysosomal conditions.

In other embodiments, a conjugate includes:

(1) a therapeutic glycoprotein (G), (2) a masking moiety (M) covalently linked to an amino acid residue of the glycoprotein through a first linker ($L^1$), and (3) a targeting moiety (T) covalently linked to the masking moiety through a second linker ($L^2$), wherein the glycoprotein is released from the conjugate under lysosomal conditions.

In some embodiments, the therapeutic glycoprotein is a lysosomal enzyme, such as, e.g., lysosomal enzymes listed in Table 2, including in particular, glucocerebrosidase, α-galactosidase A, acid α-glucosidase, or acid sphingomyelinase. In some embodiments, the therapeutic glycoprotein is glucocerebrosidase or α-galactosidase A.

In some embodiments, $L^1$ and/or $L^2$ comprise(s) one or more labile groups such as, e.g., a hydrazone and/or a disulfide group, that allow for a biologically active glycoprotein to be released at the site of action in the cells, e.g., in the lysosome.

In some embodiments, the masking moiety is a polymer selected the group consisting of polyethylene glycol (PEG), polyvinylpyrrolidone (PVP), polymethacrylate (PMA), polysialic acid (PSA), hyaluronic acid (HA), hydroxy alkyl starches (HAS), albumin, and dextran.

The invention further encompasses methods of making and using the conjugates of the inventions. The conjugates can be used, for example, as pharmaceutical compositions, e.g., for treatment of lysosomal storage disorders listed in Table 2. In some embodiments, the lysosomal storage disorder is Fabry, Gaucher, Pompe or Niemann Pick B disease.

BRIEF DESCRIPTION OF THE SEQUENCES

TABLE 1

Sequences appearing in the Sequence Listing

Figure 1:
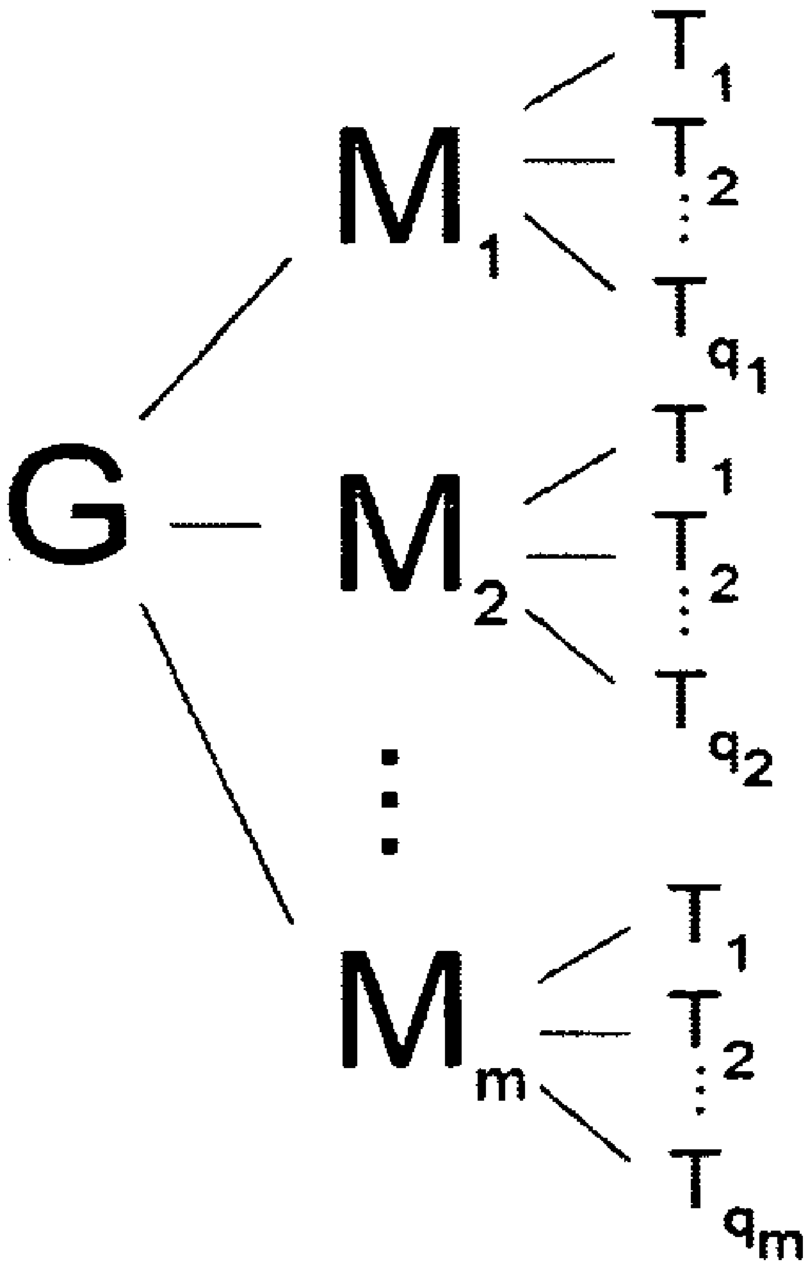
FIG. 1 depicts a structural representation of a nonlimiting embodiment of the invention. G, M, and T denote a glycoprotein, a masking moiety, and a targeting moiety, respectively. Linkers $L^1$ and $L^2$ are not shown.

| SEQ ID NO | Sequence | Description |
|---|---|---|
| SEQ ID NO:1 | GKKKKKKKKKGC-amide | K9 |
| SEQ ID NO:2 | CF-GGGYGRKKGGQRRRGGGC-amide | Tat* |
| SEQ ID NO:3 | CF-GGGGGKGGGKGGGGGC-amide | K2 |
| SEQ ID NO:4 | CF-GGGKKKKKKKKKGGGC-amide | K9 |
| SEQ ID NO:5 | CF-GGGkkkkkkkkkGGG-amide | k9** |
| SEQ ID NO:6 | Biotin-GRRRRRRRRRGC-OH | R9 |
| SEQ ID NO:7 | THRPPMWSPVWP | |
| SEQ ID NO:8 | ASSLNIA | |
| SEQ ID NO:9 | CKGGRAKDC | |
| SEQ ID NO:10 | GETRAPL | |

*CF-carboxyfluorescein;
**k-(D) lysine.

DETAILED DESCRIPTION OF THE INVENTION

Ternary Conjugates

The present invention provides ternary conjugates comprising:

(1) a therapeutic glycoprotein (G), (2) at least one masking moiety (M) covalently linked to the glycoprotein through a first linker ($L^1$), and (3) at least one targeting moiety (T) covalently linked to the masking moiety through a second linker ($L^2$), wherein the therapeutic glycoprotein is released from the conjugate under lysosomal conditions thereby yielding a biologically active glycoprotein at the site of action in the cell, e.g., in the lysosome.

In one embodiment, the conjugate comprises:

(1) a therapeutic glycoprotein (G), (2) at least one masking moiety (M) covalently linked to an oligosaccharide side chain of the glycoprotein through a first linker ($L^1$), and (3) at least one targeting moiety (T) covalently linked to the masking moiety through a second linker ($L^2$), wherein the therapeutic glycoprotein is released from the conjugate under lysosomal conditions thereby yielding a biologically active glycoprotein at the site of action in the cell, e.g., in the lysosome.

In another embodiment, the conjugate comprises:

(1) a therapeutic glycoprotein (G), (2) at least one masking moiety (M) covalently linked to an amino acid residue of the glycoprotein through a first linker ($L^1$), and (3) at least one targeting moiety (T) covalently linked to the masking moiety through a second linker ($L^2$), wherein the therapeutic glycoprotein is released from the conjugate under lysosomal conditions thereby yielding a biologically active glycoprotein at the site of action in the cell, e.g., in the lysosome.

The term "biologically active" refers to a function or set of functions (or the effect to which the function is attributed) performed by a molecule in a biological system in vivo or in vitro. Biological activity may be assessed by, for example, enzymatic activity or inhibitory activity as described in the Examples.

The release of the therapeutic glycoprotein may occur as a result of degradation of $L^1$, M, or both at the site of action. Optionally, $L^2$ may also be degradable at the site of action.

In some embodiments, the ternary conjugates are rapidly degradable at the site of action in a cell. The term "rapidly degradable" means that up to 50%, 60%, 70%, 80%, 90%, or substantially all of the glycoprotein is released from the conjugate within 48 hours under lysosomal conditions. (The time can be measured from the time of the administration to a subject or from the time of intracellular uptake). In such embodiments, the half-life of the conjugate (the time at which 50% of the administered glycoprotein is released) is less than 48 hours, e.g., about 6, 12, 18, 24, 30, 36, 42, and 46 hours. The conjugate can be rapidly degradable due to the masking moiety or a linker, or both.

The term "lysosomal conditions" refers to conditions within the lysosome. The lysosome is a cytoplasmic organelle which, when isolated under appropriate conditions, displays one or more lysosomal hydrolase activities. Lysosomal isolation procedures are described in e.g., Bonifacino et al. (eds.) Current Protocols in Cell Biology, John Wiley & Sons, Inc., 2002, section 3.6. In general, the lysosomal conditions may be reproduced in vitro and include a pH of about 4.5-5.5 and a reducing environment as illustrated in the Examples.

In other embodiments, the ternary conjugates are slowly degradable at the site of action in a cell. The term "slowly degradable" means that less than 50%, 40%, 30%, 20%, 10% or substantially none of the glycoprotein is released from the conjugate after approximately 48 hours under lysosomal conditions. In such embodiments, the half-life of the conjugate is more than 48 hours, e.g., 50, 96, 168, 216, 240, 360, or 480 hours. The conjugate can be slowly degradable due to the masking moiety or a linker, or both.

The ternary conjugates of the invention may comprise as many as 20 masking moieties (M), each independently linked to at least one and as many as 20 targeting moieties (T). Generally, a conjugate of the invention or a part thereof has the following formula:

$$G(L^1\text{-}M(L^2\text{-}T)_n)_m \quad \text{(I)}$$

where n and m are integers; and $1 \leqq n \leqq 20$ and $1 \leqq m \leqq 20$, independently of each other. n and/or m may, for example, be chosen from 2 to 16, 4 to 12, 1 to 8, or 2 to 4. For example, a particular conjugate molecule may comprise two masking moieties M, with one of the two masking moieties comprising 4 targeting moieties, while the other masking moiety may comprise 12 targeting moieties. For illustration purposes only and without limitation, FIG. 1 provides a schematic structural representation of a hypothetical conjugate molecule containing m masking moieties and a varying number ($q_m$) of targeting moieties associated with each masking moiety (linkers are omitted from the figure). Masking moieties M may be the same or different; linkers $L^1$ may be same or different; targeting moieties T may be the same or different. Additionally, there could be one or more masking moieties that do not have any $L^2$-T or T attached thereto so long as there is at least, on average, one masking moiety that does. Similarly, there could be one or more $L^1$ that do not have any M. Thus, the ratio of number of targeting moieties to the number of masking moieties in a conjugate composition may be less than 1, e.g., as low as 0.1. Likewise, the ratio of the number of masking moieties per the number of G's in a conjugate composition may be less than 1, e.g., as low as 0.1. The embodiments with $n \geqq 2$ may provide an additional advantage of "multivalent display" of the targeting moiety, which may allow enhanced intracellular uptake under some conditions.

Glycoprotein

The term "therapeutic glycoprotein" refers to a protein that bears one or more O- and/or N-linked oligosaccharide side chain(s) such that when the glycoprotein is delivered intracellularly, it will exert a therapeutic effect such as, e.g., the prevention, delayed onset, or amelioration of symptoms in a patient or otherwise produce a desired biological outcome, such as, e.g., an improved organelle, cell, tissue, or organ function due to, for example, reduced substrate accumulation, reduced cell growth, induction of apoptosis, etc. In some embodiments, the therapeutic glycoprotein is a non-viral glycoprotein, e.g., an antibody. One class of therapeutic glycoproteins is enzymes that are deficient in a patient to be treated. Examples of such enzymes include lysosomal enzymes such as lysosomal hydrolases listed in Table 2. In some embodiments, the therapeutic glycoprotein is α-Galactosidase A, acid β-glucosidase (glucocerebrosidase), acid α-glucosidase or acid sphingomyelinase In some embodiments, the therapeutic glycoprotein is α-Galactosidase A, or acid β-glucosidase (glucocerebrosidase).

TABLE 2

Lysosomal Storage Disorders and Corresponding Glycoproteins

| Lysosomal storage disorder | Defective enzyme/Therapeutic glycoprotein |
|---|---|
| Fabry | α-Galactosidase A |
| Farber | Acid ceramidase |
| Fucosidosis | Acid α-L-fucosidase |
| Gaucher types 1, 2, and 3 | Acid β-glucosidase (glucocerebrosidase) |
| $G_{M1}$ gangliosidosis* | Acid β-galactosidase |
| Hunter | Iduronate-2-sulfatase |
| Hunter-Scheie | α-L-Iduronidase |
| Krabbe | Galactocerebrosidase |
| α-Mannosidosis | Acid α-mannosidase |
| β-Mannosidosis | Acid β-mannosidase |
| Maroteaux-Lamy | Arylsulfatase B |
| Metachromatic leukodystrophy | Arylsulfatase A |
| Morquio A | N-Acetylgalactosamine-6-sulfate sulfatase |
| Morquio B | Acid β-galactosidase |
| Niemann-Pick | Acid sphingomyelinase |
| Pompe | Acid α-glucosidase |
| Sandhoff* | β-Hexosaminidase B |
| Sanfilippo A | Heparan N-sulfatase |
| Sanfilippo B | α-N-Acetylglucosaminidase |
| Sanfilippo C | Acetyl-CoA: α-glucosaminide N-acetyltransferase |
| Sanfilippo D | N-Acetylglucosamine-6-sulfate sulfatase |
| Schindler-Kanzaki | α-N-acetylgalactosaminidase |
| Sialidosis | Sialidase |
| Sly | β-Glucuronidase |
| Tay-Sachs* | β-Hexosaminidase A |

*Diseases resulting from the storage of glycosylceramide-based glycosphingolipids.

The therapeutic glycoprotein may contain two or more subunits (such as, e.g., α-galactosidase A which is a homodimer of two 45 kDa subunits) with one or more of these subunits bearing at least one oligosaccharide chain.

Targeting Moiety

The targeting moiety is selected based on the target cell type, tissue, or organ to allow sufficiently specific delivery of the therapeutic glycoprotein to the desired target. Examples of targeting moieties include:

(1) transducing peptides such as, e.g., R9 (SEQ ID NO:6) (Mitchell et al., J. Peptide Res. (2000) 56:318-325; Wender et al., Proc. Natl. Acad. Sci. (2000) 97:13003-13008), K9 (SEQ ID NO:4) (Shen et al., Proc. Natl. Acad. Sci. (1978) 75:1872-76; U.S. Pat. No. 4,701,521), Tat (SEQ ID NO:2) (Mann et al., EMBO J. (1991) 10:1733-39; Fawell et al., Proc. Natl. Acad. Sci. (1994) 91:664-668; Schwarze et al., Science (1999) 285:1569-72), SynB1-SynB6 and sequence variants thereof (Roussele et al., Mol. Pharmacol. (2000) 57:679-686; Day et al., J. Immunol. (2003) 170:1498-1503, antennapedia (Derossi et al., Trends in Cell Biol. (1998) 8:84-87), VP22 (Elliott et al., Cell (1997) 88:223-233);

(2) natural receptor ligands such as, e.g., insulin (U.S. Pat. No. 4,749,570) for targeting through the insulin receptor, insulin-like growth factor II (IGF-II) (U.S. Patent Appln. Pub. No. 2003/0082176) for targeting through the cation-independent mannose 6-phosphate receptor (CIMPR), and receptor-associated protein (RAP) (Prince et al. J. Biol. Chem. (2004) 279:35037-35046) for targeting through LDLR-related protein (LRP), and melanotransferrin (Demeule et al. J. Neurochem. (2002) 83:924-933 for targeting through a member of the LDL receptor family to brain;

(3) phage-display selected peptide ligands such as, e.g., Sp8ca (WO 01/90139) for targeting to brain, ASSLNIA (SEQ ID NO:8) (U.S. Pat. No. 6,399,575) for targeting to muscle, CKGGRAKDC (SEQ ID NO:9) (Kolonin et al., Nature Med. (2004) 10:625-32) for targeting to adipose tissue, GETRAPL (SEQ ID NO:10) (U.S. Pat. No. 6,399,575) for targeting to muscle or brain; and THRPPMWSPVWP (SEQ ID NO:7) (Lee et al., Eur. J. Biochem. (2001) 268:2004-2012) for targeting through the transferrin receptor to the brain;

(4) fragments of endogenous proteins such as tissue factor pathway inhibitor (TFPI) (Hembrough et al., Blood (2004) 103:3374-3380) for targeting through Very Low Density Lipoprotein (VLDL) receptor;

(5) antibodies to receptors such as, e.g., the anti-transferrin receptor antibody OX26 (Frieden et al., J. Pharm. Exp. Ther. (1996) 278:1491-98; Schnyder et al., Biochem. J. (2004) 377:61-7) and other anti-transferrin receptor antibodies (Friden et al. 1996; Zhang et al., Mol. Therapy (2003) 4:1-8 for targeting to the brain; the anti-insulin receptor antibody 83-14hIRMab (Zhang et al., Mol. Therapy (2003) 7:1-8); the anti-Fc44 antibody (WO 02/057445; Muruganandam et al., FASEB J. (2002) 16:240-242);

(6) small molecules such as, e.g., bisphosphonates for targeting to bone; and (7) non-endogenous proteins and fragments thereof, such as, e.g., diphtheria toxin $CRM_{197}$, for targeting heparin-binding epidermal growth factor precursor (HB-EGF) present on the surface of cells in the heart and lung and the blood brain barrier (Gaillard P J, et al. Expert Opin. Drug Deliv. 2005 2(2): 299-309; Abraham et al. BBRC (1993) 190:125-133).

Additional targeting moieties can be made, e.g., as described in Cabilly (ed.), Combinatorial Peptide Library Protocols, 1st ed., Humana Press, 1998; Jung (ed.), Combinatorial Peptide and Nonpeptide Libraries: A Handbook, 1997, John Wiley & Sons; and Antibodies: A Laboratory Manual, Harlow et al. (eds.) Cold Spring Harbor Laboratory, 1988; and Borrebaeck (ed.) Antibody Engineering, 2nd ed., 1995, Oxford University Press.

Masking Moiety

A masking moiety is used to mask the oligosaccharide side chain of the glycoprotein from being recognized by its cognate receptor. For example, a masking moiety should be of sufficient size or bulk to reduce (or completely block) the binding of the glycoprotein to its cognate receptor by at least 30%, 40%, 50%, 60%, 70% or more. Suitable methods for measuring the reduction or blockage of the glycoprotein-receptor are illustrated in the Examples.

Examples of Masking Moieties Include the Following:

(1) non-naturally occurring biocompatible polymers such as, e.g., polyalkylene oxides, polyethylene glycol (PEG), polyvinylpyrrolidone (PVP), and polymethacrylate (PMA), polyethyleneimine (PEI), polyacrylamide, α,β-poly(N-hydroxyethyl)-DL-aspartamide (PHEA, Cavallaro et al., J. Drug Target. (2004) 12:593-605), poly(vinylpyrrolidone-co-dimethyl maleic anhydride (poly(VP-co-DMMAn) Kamada et al., Nature Biotechnology (2003) 21:399-404), N-(2-hydroxypropyl)methacrylimide) (HMPA, Etrych et al., J. Controlled Release (2001) 73:89-102.)

(2) polyanionic polysaccharides such as, e.g., polysialic acids (PSA) (e.g., colomininic acid), hyaluronic acid (HA), and dextran sulfate; and hydroxy alkyl starches (e.g., hydroxy methyl starch, hydroxy ethyl starch, hydroxy propyl starch, etc.).

(3) proteinaceous polymers such as, e.g., albumin (e.g., human serum albumin (HSA), immunoglobulin (IgG).

In some embodiments, the masking moiety is rapidly degradable under lysosomal conditions. The term "rapidly degradable" when used in reference to a masking moiety means that the masking moiety is degraded so that up to 50%, 60%, 70%, 80%, 90%, or substantially all of the glycoprotein is released from the conjugate within 48 hours thereby yielding a biologically active glycoprotein at the site of action in the cell. In such embodiments, the half-life of the release is less than 48 hours, e.g., about 6, 12, 18, 24, 30, 36, 42, and 46 hours. Rapidly degradable masking moieties may be synthesized from, e.g., PSA or HA.

In other embodiments, the masking moiety is "slowly degradable" under the lysosomal conditions, i.e., it is more resistant to degradation and provides for a more prolonged supply of biologically active glycoprotein at the site of action in the cell. The term "slowly degradable" when used in reference to a masking moiety means that the masking moiety is degraded so that less than 50%, 40%, 30%, 20%, 10% or substantially none of the glycoprotein is released from the conjugate after approximately 48 hours under the lysosomal conditions. In such embodiments, the half-life of the release is more than 48 hours, e.g., 50, 96, 168, 216, 240, 360, or 480 hours. Slowly degradable masking moieties may be synthesized from, e.g., PEG, PVP, or hydroxyethyl starch.

The masking moiety may have a molecular weight of, for example, 0.5-100, 1-50, or 10-20 kDa. The masking moiety may comprise one or more (e.g., 2 to 40, 2 to 20, 2 to 10, 3, 4, or 5) functional groups for conjugation to the glycoprotein and the targeting moiety. For example, when the masking moiety is PEG, the PEG may comprise multiple arms in either a pendant or star configuration, such as a pendant 8- or 16-arm PEG, or a star configuration 4- or 6-arm PEG, or block copolymers containing PEG groups such as described in, e.g., Funhoff et al., J. Control. Release (2005) 102:711-724; Lecolley et al. Chem. Comm. (2004) 18:2026-2027.

Linkers

The linkers $L^1$ and $L^2$ serve to covalently bind the masking moiety to the glycoprotein and the targeting moiety, respectively. In some embodiments, $L^1$ and/or $L^2$ each comprises a labile group that allows for the therapeutic glycoprotein to be released from the conjugate under lysosomal conditions thereby yielding a biologically active glycoprotein at the site of action in the cell.

In some embodiments, $L^1$ and/or $L^2$ are/is rapidly degradable under lysosomal conditions. The term "rapidly degradable", when used in reference to a linker, means that the linker is degraded so that up to 50%, 60%, 70%, 80%, 90%, or substantially all of the glycoprotein is released from the conjugate within 48 hours thereby yielding a biologically active glycoprotein at the site of action in the cell. In such embodiments, the half-life of the release is less than 48 hours, e.g., about 6, 12, 18, 24, 30, 36, 42, and 46 hours. Rapidly degradable linkers include, for example, hydrazones and disulfides.

In other embodiments, $L^1$ and/or $L^2$ are/is "slowly degradable" under the lysosomal conditions, i.e., they are more resistant to degradation and provide for a more prolonged supply of biologically active glycoprotein at the site of action in the cell. The term "slowly degradable", when used in reference to a linker, means that the linker degraded so that less than 50%, 40%, 30%, 20%, 10% or substantially none of the glycoprotein is released from the conjugate after approximately 48 hours under the lysosomal conditions. In such embodiments, the half-life of the release is more than 48 hours, e.g., 50, 96, 168, 216, 240, 360, or 480 hours.

The linkers $L^1$ and $L^2$ are each independently chosen preferably from alkyl (e.g., 1 to 6 carbons), carbonyl, hydrazone, disulfide, heteroaryl, and amido, but additionally may be chosen from alkyl, carbonyl, thiocarbonyl, ether, thioether, ester, disulfide, amino, amido, imino, thioamido, sulfonamido, sulfide, hydrazone, aryl, heteroaryl, cycloalkyl, and heterocyclyl. Any of these groups can be unsubstituted or substituted with one or more functional groups such as aldehyde, alkoxy, amido, amino, aryl, carboxy, cyano, cycloalkyl, ester, ether, halogen, heterocyclyl, hydroxy, ketone, nitro, sulfonate, sulfonyl, or thiol. In some embodiments, alkyl is substituted with a carboxylic acid or an ester thereof. In other embodiments, the ether is a polyether such as a polyalkylene oxide, e.g., polyethylene oxide.

In some embodiments, $L^1$ and/or $L^2$ comprise(s) the hydrazone group of formula (IIa):

(IIa)

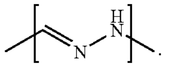

In other embodiments, $L^1$ and/or $L^2$ comprise(s) the disulfide group of formula (IIb):

(IIb)

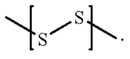

In some embodiments, $L^1$ and/or $L^2$ comprise a hydrazone-containing group selected from formulas (III)-(VIII):

(III)

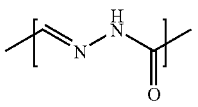

(IV)

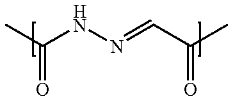

(V)

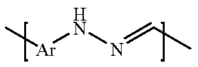

(VI)

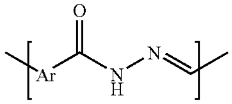

(VII)

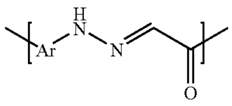

(VIII)

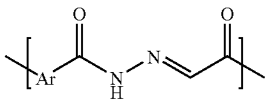

wherein Ar is aryl, heteroaryl, or pyridyl such as, for example:

(IX)

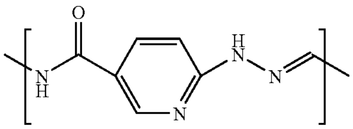

(X)

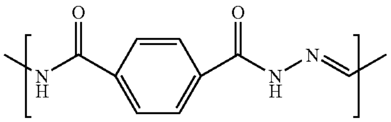

(XI)

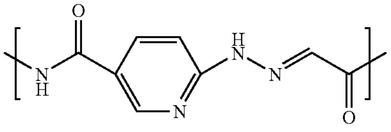

(XII)

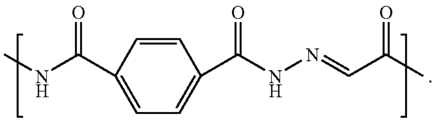

In some embodiments, $L^1$ may contain 0, 1, or 2 hydrazone groups of formula (II) and 0 or 1 disulfide groups, while in the same conjugate $L^2$ may contain 0 or 1 hydrazones and 0 or 1 disulfide groups. Examples of various specific embodiments are provided in Table 3. In some embodiments, for example, $L^1$ and $L^2$ each independently include 1, 2, or more hydrazone groups and additionally a disulfide.

TABLE 3

Examples of The Number and Type of Labile Groups in Linkers $L^1$ and $L^2$

| $L^1$ | | $L^2$ | |
|---|---|---|---|
| Hydrazone | —S—S— | Hydrazone | —S—S— |
| 0 | 0 | 0 | 0* |
| 1 | 1 | 1 | 1 |
| 1 | 1 | 1 | 0 |
| 1 | 1 | 0 | 0 |
| 1 | 0 | 0 | 0 |
| 1 | 0 | 1 | 0 |
| 2 | 1 | 1 | 0 |
| 2 | 1 | 0 | 1 |
| 2 | 1 | 1 | 1 |
| 1 | 0 | 1 | 1 |
| 1 | 1 | 0 | 1 |

*In the case of (0, 0, 0, 0), M is a masking moiety degradable under the lysosomal conditions; in all other cases, this is optional.

For example, $L^1$ and $L^2$ each independently may comprise a group selected from formulas (XIII)-(XVIII):
(XIII)
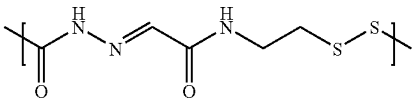
(XIV)
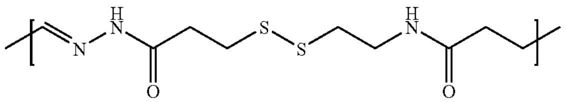
(XV)
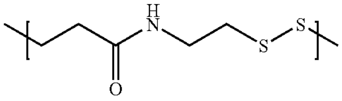
(XVI)
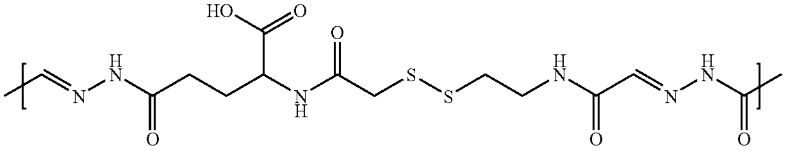
(XVII)
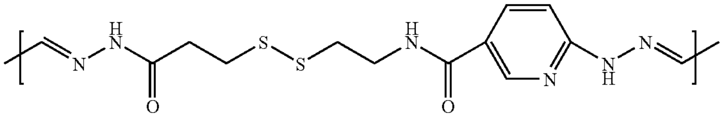
(XVIII)
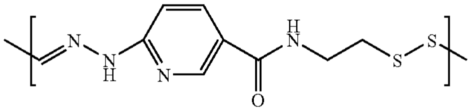
(XIX)
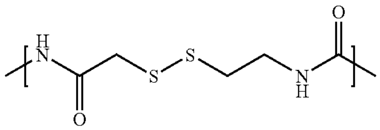
(XX)
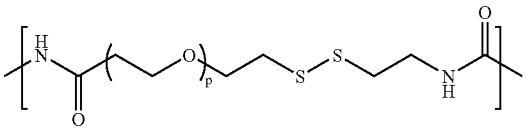
,
wherein p is an integer: 2≦p≦12.
In some embodiments, the conjugates have a formula as shown in (XIX)-(XXIII):
(XXI)
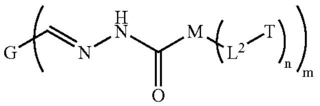
(XXII)
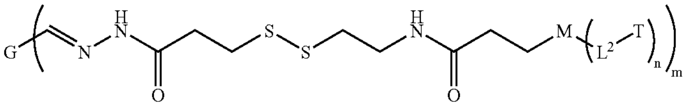
(XXIII)
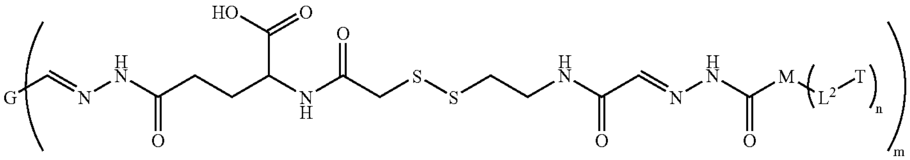
(XXIV)
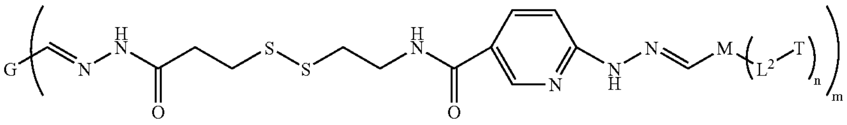

-continued (XXV)

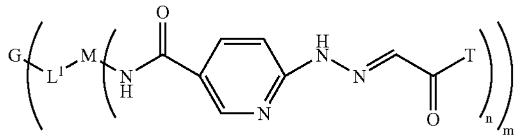
.

In other embodiments, the conjugates have a formula as shown in (XXIV)-(XXVIII):

(XXVI)

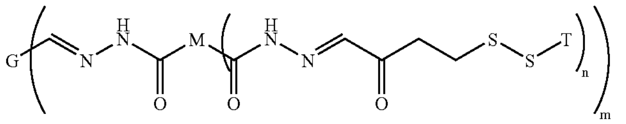

(XXVII)

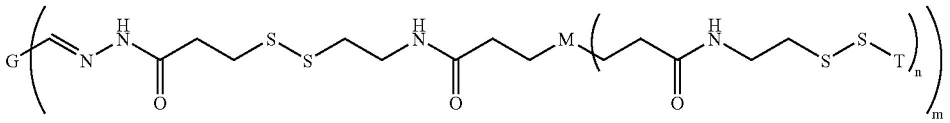

(XXVIII)

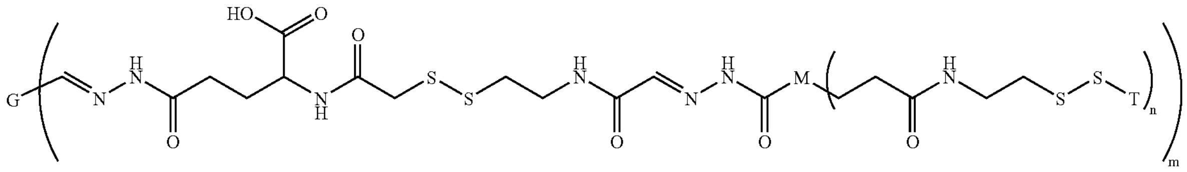

(XXIX)

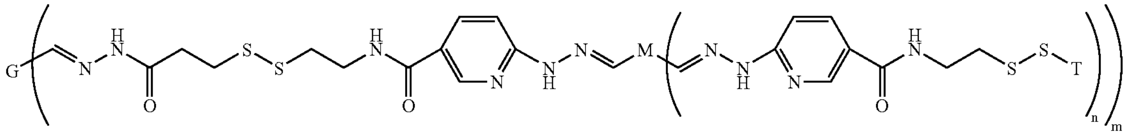

(XXX)

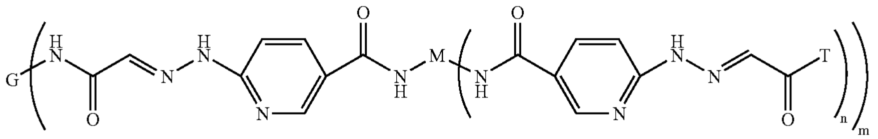

(XXXI)

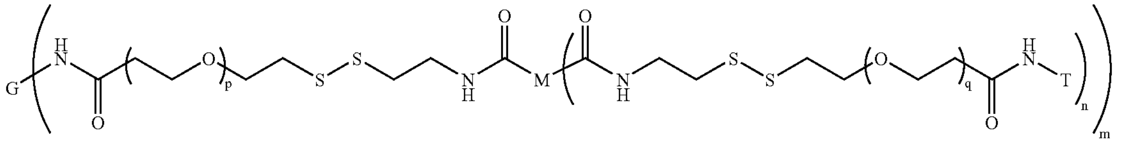
, wherein p and q are integers; and 2≦p≦12 and 2≦q≦12 independently of each other.

Methods of Making Conjugates

Methods of making conjugates of the invention, including those with formulas (I) and (XVII)-(XVI), comprise: (a) providing a masking moiety comprising a first functional group and a second functional group, (b) reacting the first functional group of the masking moiety with the oligosaccharide side chain of a therapeutic glycoprotein, and (b) reacting the second functional group with a targeting moiety.

The masking moiety may contain a single type of functional group, or it may be heterofunctional, i.e., it contains at least two different types of functional groups. For example, the masking moiety may be PEG that bears any one, any two, or more functional group(s) selected from: hydrazide, hydrazine, amine, hydroxyl, carboxylic acid, ester, thiol, maleimide, acrylate, and vinyl sulfone.

In some embodiments, the methods of making conjugates of the invention comprise: (a) reacting an oligosaccharide side chain of glycoprotein G with masking moiety M to form glycoprotein-masking moiety conjugate, and (b) reacting targeting moiety T with the glycoprotein-masking moiety conjugate to form ternary conjugate $G(L^1\text{-}M(L^2\text{-}T)_n)_m$. Alternatively, targeting moiety T may be reacted first with masking moiety M to form a "ligand-decorated" masking moiety, which is then reacted with an oligosaccharide side chain of glycoprotein G to form ternary conjugate $G(L^1\text{-}M(L^2\text{-}T)_n)_m$.

In some embodiments, an excess molar amount of the masking moiety (ligand-decorated or not) is reacted with the activated glycoprotein (e.g., more than 1, 2, 5, or 10 molar equivalents excess).

Activation of Glycoproteins

In some embodiments, a glycoprotein is activated prior to conjugation by introducing a reactive group at the linkage site on the oligosaccharide side chain of the glycoprotein. For example, the activated glycoprotein may bear an electrophilic functional group, e.g., an aldehyde group, at the linkage site, while the masking moiety (ligand-decorated or not) bears a nucleophilic functional group (e.g., hydrazide) reactive to the electrophilic group. The activated glycoprotein may further be modified to bear a nucleophilic functional group (e.g., a thiol group) by incorporating an adaptor molecule covalently linked to the oligosaccharide, while the masking moiety (ligand-decorated or not) can be made to bear an electrophilic functional group (e.g., thiol reactive group). The thiol-reactive group can be an aryl or heteroaryl disulfide (for example, a pyridyl disulfide). For example, an adaptor molecule, such as nipsylethylamine (NEA; see, e.g., U.S. Pat. No. 6,749,685) or glyoxyl-nipsylethylamide (GNEA) may be reacted with the masking moiety to form a pyridyl disulfide. In other embodiments, the thiol reactive-group can be an aryl or heteroaryl disulfide, vinyl sulfone, vinyl acetate, or maleimide.

Glycoprotein activation may be accomplished either by oxidizing sialic acid and/or other residues (e.g., using periodate), or by first exposing galactose residues through the removal ("trimming") of the terminal sialic acid groups (e.g., using an enzyme such as neuraminidase) which is then followed by oxidation of the exposed galactose to produce a glycoprotein functionalized with an aldehyde (e.g., using an enzyme such as galactose oxidase (GAO)).

Incorporation of a Hydrazone Group

Figure 2:
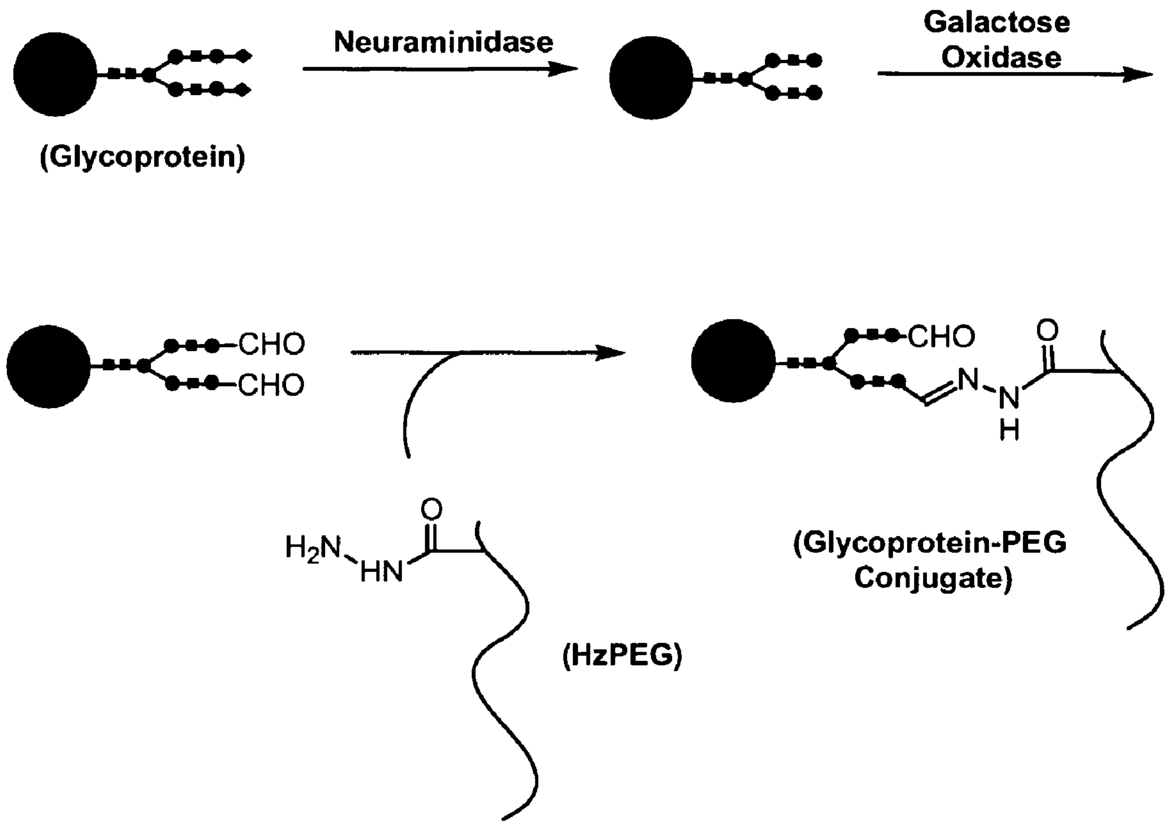
FIG. 2 depicts a scheme for conjugating a therapeutic glycoprotein to a hydrazide-PEG. Terminal sialic acids on the glycoprotein are removed by treatment with neuraminidase. The exposed terminal galactose residues are then oxidized to aldehydes by treatment with *Dactylium dendroides* galactose oxidase. Alternatively, aldehydes may be introduced through oxidation with sodium periodate. The product is then exchanged into buffer around pH 5.5 and reacted with a hydrazide PEG to form a hydrazone conjugate. The products are purified away from unreacted PEG (e.g., by anion exchange or size-exclusion chromatography).
Figure 4A:
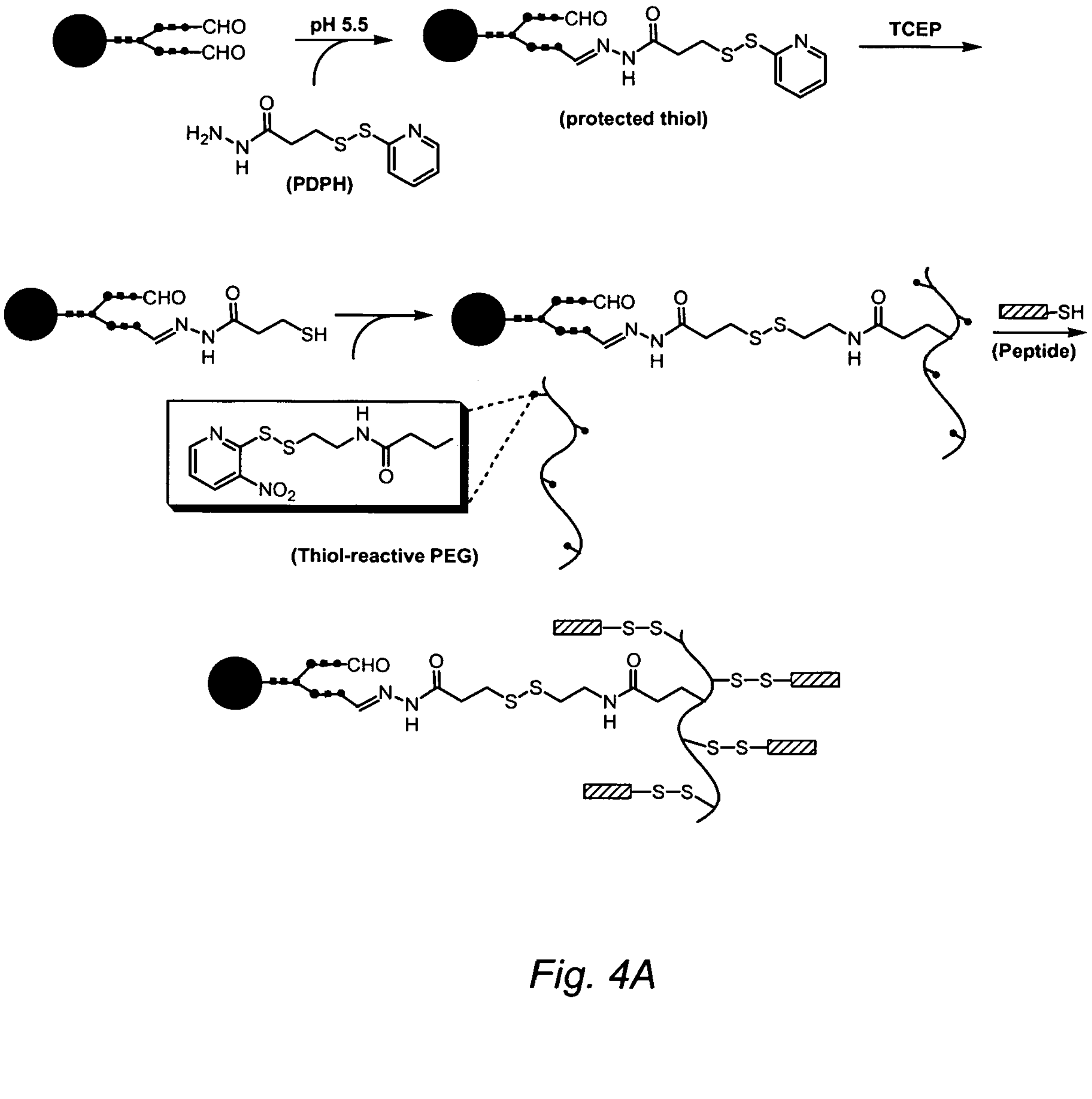
FIG. 4A illustrates the generation of a peptide-PEG-glycoprotein conjugate using thiol/hydrazide chemistry. Aldehyde groups are generated on the glycoprotein by treatment with periodate or galactose oxidase (GAO) as in FIG. 1. The GAO-treated protein is reacted with an adaptor containing a hydrazide and a protected thiol, such as 3-(2-pyridyldithio)propionyl hydrazide (PDPH). The adaptor's disulfide is then reduced (e.g., with tris-carboxyethylphosphine, TCEP) to expose the thiol, which is then reacted with a PEG molecule bearing thiol-reactive moieties. The resulting conjugate is purified (e.g., by ion-exchange chromatography) and reacted with peptides containing a cysteine moiety to yield a final ternary peptide/PEG/glycoprotein conjugate.

In some embodiments, an aldehyde is reacted with masking moiety M (see, e.g., FIG. 2 and Example 1) or an adaptor molecule (see, e.g., FIG. 4 and Example 7), wherein the masking moiety and the adaptor molecule bear a reactive hydrazine group, e.g. a hydrazide. An activated glycoprotein bearing an aldehyde group is exchanged into a buffer with a pH of about 5.5 (e.g., 5-6) and reacted with the hydrazide group. For example, as illustrated in FIG. 2, hydrazide PEG (HzPEG; available commercially from, e.g., SunBio) is used to form a hydrazone-containing conjugate. In other embodiments, the adaptor molecule contains a thiol. For example, as shown in FIG. 4, the adaptor molecule 3-(2-pyridyldithio) propionyl hydrazide (PDPH) contains a protected thiol. A similar adaptor molecule bearing a hydrazide group, such as S-acetylthioacetimide glutamic acid hydrazide (SATAGH, formed by reacting N-succinimidyl-S-acetylthioacetate (SATA) with glutamic acid γ-hydrazide (SATA; Duncan et al., Anal. Biochem. (1983) 132:68-73) can be used. The products are then purified away from unreacted PEG or adaptor, e.g., by anion exchange or size-exclusion chromatography.

Incorporation of a Disulfide Group

One method of attaching a therapeutic glycoprotein and a masking moiety (whether ligand-decorated or not) comprises: (a) incorporating a protected thiol into an oligosaccharide side chain of an activated glycoprotein using an adaptor molecule bearing a protected thiol; (b) deprotecting the thiol and reacting it with a thiol-reactive group on the masking moiety. For example, as illustrated in FIG. 4, a glycoprotein is first reacted with an adaptor molecule bearing a protected thiol, such as PDPH. Alternatively, an adaptor molecule bearing a protected thiol group may be prepared by reacting SATA with glutamic acid hydrazide to form SATAGH, which may then be reacted with a glycoprotein. The adaptor's thiol group may then be deprotected (e.g., by reduction of the disulfide with tris-carboxyethylphosphine (TCEP), or by treatment of the thioacetate with hydroxylamine) to expose the thiol, which may then be reacted with a PEG bearing thiol-reactive groups.

Figure 3:
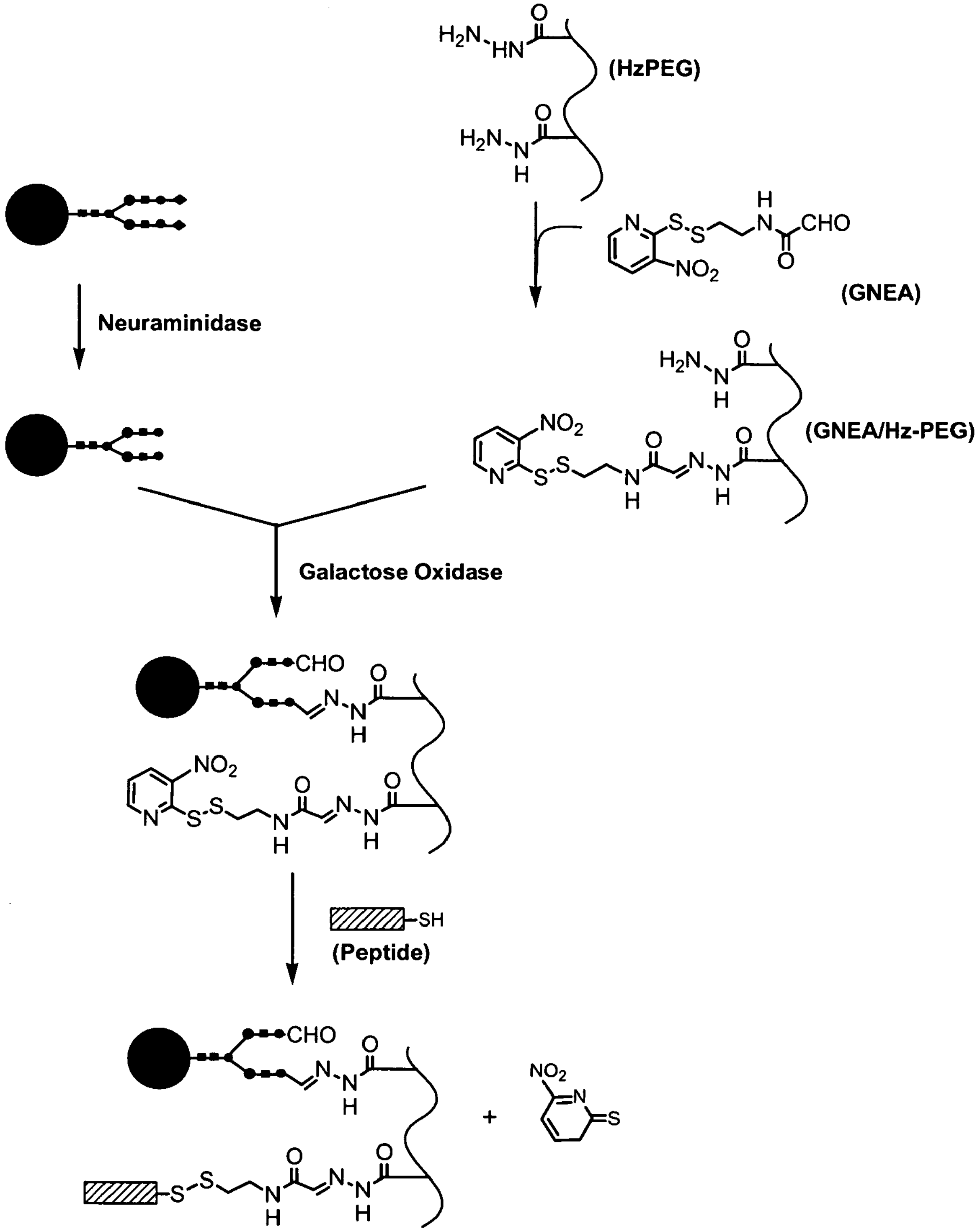
FIG. 3 shows a scheme for generating a peptide-PEG-glycoprotein conjugate using a heterobifunctional PEG. A heterobifunctional PEG is generated by reacting a hydrazide-functionalized PEG with an adaptor molecule (glyoxyl-nipsylethylamide, "GNEA") containing a hydrazide-reactive glyoxyl aldehyde linked to a thiol reactive functional group (nipsylethylamine, "NEA"). This PEG is reacted in the presence of galactose oxidase with neuraminidase-treated protein to produce a conjugate in which the PEG is coupled through a hydrazone linkage to an exposed protein oligosaccharide. This product is purified, and then coupled to a peptide containing a free thiol.

The thiol reactive group on the masking moiety may be, for example, a disulfide. In some embodiments, a disulfide may be incorporated into PEG using an adaptor molecule. For example, HzPEG can be reacted with GNEA to form GNEA-PEG (FIG. 3). Alternatively, a thiol-reactive PEG can be made by reacting NEA with PEG-bearing carboxylic acid groups (FIG. 4). The resulting conjugate may be purified (e.g., by ion-exchange chromatography) and further reacted with a targeting moiety containing a thiol group (e.g., cysteine in a peptide) to yield a final ternary glycoprotein/masking moiety/targeting moiety conjugate.

Incorporation of Hydrazone and Disulfide Groups

The methods described in the previous two paragraphs can provide linkers bearing both a hydrazone and a disulfide, for example, by using an adaptor molecule comprising both a reactive hydrazide and a protected thiol. For example, as illustrated in FIG. 4, a glycoprotein is reacted with the adaptor molecule PDPH, which bears both a protected thiol group and a hydrazide group. Alternatively, instead of PDPH, a similar adaptor molecule such as SATAGH can be used. As indicated by Duncan et al., Anal. Biochem. (1983) 132, 68-73, the protecting acetyl group in SATA can be released by hydroxylamine under selective conditions to expose the thiol, which is then available to react with NEA under conditions in which less than 20% hydrolysis of the NEA occurs from direct hydroxylamine attack.

In other embodiments, such as those illustrated in FIG. 4, an adaptor molecule containing a stabilized hydrazine group such as, e.g., pyridyl hydrazide, (and optionally a thiol reactive group) is used to conjugate the glycoprotein to the masking moiety. Examples of such adaptor molecules include the HydraLink™ reagents (SoluLink Biosciences) as described, e.g., in U.S. Pat. Nos. 5,206,370; 5,420,285; 5,753,520; and 5,769,778 and European Patent No. 384,769). For example, PEG-amine can be reacted with an N-hydroxysuccinimide ester of a pyridyl hydrazine (succinimidyl 4-hydrazinonicotinate acetone hydrazone, "SANH") or terephthalic acid hydrazide (succinimidyl 4-hydrazidoterephthalate hydrochloride, "SHTH") to generate a PEG-pyridyl hydrazine or a PEG-terephthalic acid hydrazide. The PEG-pyridyl hydrazine or -terephthalic acid hydrazide can be reacted with a galactose oxidase treated glycoprotein to yield a hydrazone. Alternatively, a thiol reactive group may be incorporated into the stabilized hydrazine by first reacting SANH or SHTH with NEA. The resulting product may be reacted with a masking moiety containing a reactive carbonyl, such as a polyanionic polysaccharide (e.g., PSA) to form a hydrazone.

The glycoprotein/masking moiety conjugate is then further reacted with a targeting moiety. In some embodiments, the targeting group can be conjugated to the masking moiety via a hydrazone linkage as illustrated in FIG. 3. Alternatively, in the case of the targeting moiety being a peptide comprising an N-terminal serine or threonine, the peptide may be oxidized, e.g. with sodium periodate, to yield a glybxyl peptide derivative. A glycoprotein/masking moiety conjugate comprising a hydrazine may be made, for example, by reacting PEG-amine with SANH or SHTH, followed by reaction with a galactose oxidase treated glycoprotein. The glyoxyl peptide derivative may then be reacted with the pyridyl hydrazine or benzoic acid hydrazide groups on the a glycoprotein/masking moiety conjugate to yield a ternary conjugate in which the targeting moiety is linked via a hydrazone group. In other embodiments, a targeting moiety that bears a thiol (e.g., cysteine in a peptide) can be reacted with a thiol-reactive group, for example a disulfide group in an adaptor molecule as illustrated in FIG. 4.

Conjugation with an Amino Acid Residue of a Glycoprotein

In many cases, conjugation of a masking moiety to an oligosaccharide will produce a high degree of masking of the oligosaccharide and inhibition of receptor binding and clearance. However, as will be appreciated by those of ordinary skill in the art, the distribution of glycosylation sites in the three-dimensional structure of glycoproteins may not always provide an optimal placement for masking critical oligosaccharide determinants from receptor binding. For example, high mannose oligosaccharides may be uniquely positioned and at a significant distance from the sites of the complex oligosaccharides, which are amenable to the conjugation chemistry described above.

Accordingly, in another embodiment, methods of making conjugates of the invention comprise: (a) providing a masking moiety comprising a first functional group and a second functional group, (b) reacting the first functional group of the masking moiety with an amino acid residue of a therapeutic glycoprotein, and (c) reacting the second functional group with a targeting moiety.

The methods described above for forming a conjugate of the invention via an oligosaccharide side chain of the glycoprotein may be also be used to form a conjugate via an amino acid residue of the glycoprotein.

Additionally, in some embodiments, the methods of making conjugates of the invention comprise: (a) reacting an amino acid residue of glycoprotein G with masking moiety M to form a glycoprotein-masking moiety conjugate, and (b) reacting targeting moiety T with the glycoprotein-masking moiety conjugate to form ternary conjugate $G(L^1\text{-}M(L^2\text{-}T)_n)_m$. Alternatively, targeting moiety T may be reacted first with masking moiety M to form a "ligand-decorated" masking moiety, which is then reacted with an amino acid residue of glycoprotein G to form ternary conjugate $G(L^1\text{-}M(L^2\text{-}T)_n)_m$.

In some embodiments, an amino acid residue is activated prior to conjugation by introducing a reactive group on to the amino acid. For example, an amino acid residue of the glycoprotein may be activated to bear a nucleophilic functional group while the masking moiety may bear an electrophilic functional group. In some embodiments, the glycoprotein may be modified to bear a nucleophilic functional group (e.g., a thiol) by incorporating an adaptor molecule covalently linked to the amino acid residue, while the masking moiety can be made to bear and electrophilic functional group (e.g., a thiol-reactive group). In other embodiments, the amino acid residue may be activated to bear an electrophilic functional group, while the masking moiety may bear a nucleophilic group.

In some embodiments, an excess molar amount of the masking moiety (ligand-decorated or not) is reacted with the amino acid residue or activated amino acid residue of a glycoprotein (e.g., more than 1, 2, 5, or 10 molar equivalents excess).

Figure 4B:
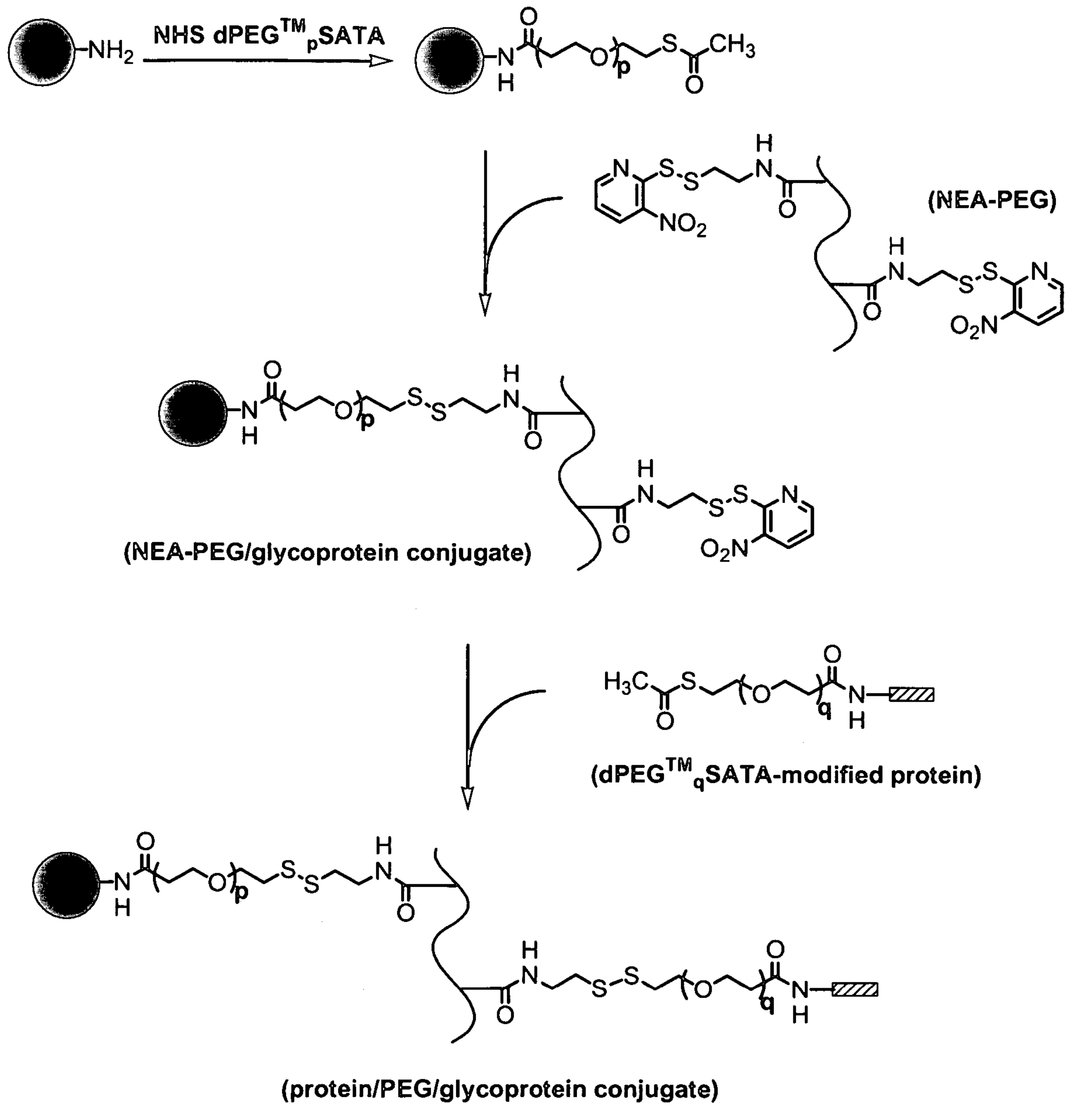
FIG. 4B illustrates conjugation of the glycoprotein through an amino acid residue. An amino acid residue, in this illustration a lysine, is reacted with S-acetyl-$dPEG^{tm}{}_p$ NHS ester to introduce a thiol group on the glycoprotein. The acetyl-protected thiol is deprotected with hydroxylamine and reacted with an NEA-PEG to produce a disulfide linked NEA-PEG/glycoprotein conjugate. A targeting moiety bearing a protected thiol, such as a protein modified with S-acetyl-$dPEG^{tm}{}_q$ NHS ester, is deprotected and reacted with the NEA-PEG/glycoprotein conjugate to produce the final ternary protein/PEG/glycoprotein conjugate.

In one embodiment, the amino acid residue to which the masking moiety is linked is a lysine. The lysine may be modified with an adaptor molecule to introduce a reactive group, such as a thiol. For example, the lysine residue may be reacted with a thiolation reagent, such as iminothiolane (Traut's reagent), or N-succinimidyl-S-acetylthioacetate (SATA, Duncan, R. J. S. et al. (1983) Anal. Biochem. 132, 68-73). In one embodiment, the thiolation reagent contains spacers, such as SATA-type reagents containing a PEG linker such as S-acetyl-dPEG™$_4$ NHS ester (dPEG™$_4$ SATA) and S-acetyl-dPEG™$_8$ NHS ester (dPEG™$_8$ SATA) (Quanta Biodesign). The thiol (after deprotection, if necessary) may be reacted with a thiol-reactive masking moiety to form a glycoprotein-masking moiety conjugate. For example, the thiol-modified amino acid residue may be reacted with an NEA-PEG to form a disulfide linked glycoprotein-masking moiety conjugate (FIG. 4B). The glycoprotein in such disulfide linked conjugates will be susceptible to release from the masking moiety in the strongly reducing environment of a lysosome.

In one embodiment, the thiolation reagent is SATA. In another embodiment, the thiolation reagent is a SATA-type reagent containing a PEG linker wherein the PEG linker is between 2 and 12 ethylene glycol units in length, or between 4 and 8 ethylene glycol units in length, such as dPEG™$_4$ SATA or dPEG™$_8$ SATA, respectively.

After reaction of the thiol-modified amino acid residue with the thiol reactive masking moiety, the resulting conjugate may be purified, for example, by ion exchange chromatography. The conjugate may then be reacted with a thiol-containing targeting moiety to form the ternary conjugate. The targeting moiety may be a peptide or protein containing a cysteine residue. Where the targeting moiety does not contain a cysteine residue, one may be introduced into the protein or peptide sequence or a thiol may be introduced by chemical conjugation as described for the glycoprotein. The ternary conjugate may be purified by size-exclusion chromatography or by other means.

Use of a Heterobifunctional Masking Moiety

Yet another method of making ternary conjugates of the invention involves the use of a heterobifunctional masking moiety, for example, a masking moiety which comprises a nucleophile such as, e.g., an aldehyde-reactive group, as a first functional group and an electrophile such as, e.g., a thiol-reactive group, as second functional group. Such a method comprises: (a) reacting the heterobifunctional masking moiety with an aldehyde group on the oxidized oligosaccharide side chain of a glycoprotein and (b) reacting a thiol group of a targeting moiety with the thiol-reactive on the masking moiety. (See, e.g., FIG. 3).

In some embodiments, a heterobifunctional masking moiety is prepared from a masking moiety bearing two or more aldehyde-reactive groups, e.g., hydrazide groups (e.g., HzPEG in FIG. 3). As illustrated in FIG. 3, a hydrazide-functionalized PEG is reacted with a molecule containing a hydrazide-reactive glyoxyl aldehyde and a thiol-reactive functional group, such as GNEA, to form a heterobifunctional PEG containing a hydrazide group and a thiol reactive group. This heterobifunctional PEG is reacted in the presence of galactose oxidase with a neuraminidase-treated glycoprotein to produce a conjugate in which the PEG is coupled through a hydrazone linkage to an exposed protein oligosaccharide. This product is purified, and then coupled to a peptide containing a free thiol.

Uses of Conjugates

Conjugates of invention can be used as therapeutics in pharmaceutical compositions for treatment of mammals (e.g., human and non-human animals). If necessary, the therapeutic effect of a conjugate may be tested using suitable assays such as described in the Examples and/or in vivo animal models (e.g., described in Jeyakumar et al., Neuropath. Appl. Neurobiol. (2002) 28:343-357; Mizukami et al., J. Clin. Invest. (2002) 109:1215-1221; Raben et al., J. Biol. Chem. (1998) 273(30):19086-92; Marshall et al. Mol. Ther. (2002) 6(2):179-89; Ohshima et al. Proc. Nat. Acad. Sci. (1997) 94(6):2540-4; Horinouchi et al. Nat. Genet. (1995) 10(3):288-93; McEachern et al. J. Gene Med. (2006 Mar. 10) (Epub ahead of print)). The data obtained from cell culture assays or animal studies can be used in formulating dosage ranges of for use in humans. Therapeutically effective dosages achieved in one animal model can be converted for use in another animal, including humans, using conversion factors (e.g., Equivalent Surface Area Dosage factor) known in the art (see, e.g., Freireich et al. (1966) Cancer Chemother. Reports, 50(4):219-244).

Pharmaceutical compositions will comprise a conjugate of the invention and one or more suitable pharmaceutical excipients. Various pharmaceutical excipient formulations are well known (see, e.g., Physicians' Desk Reference (PDR) 2003, 57th ed., Medical Economics Company, 2002; and Gennado et al. (eds.), Remington: The Science and Practice of Pharmacy, 20th ed, Lippincott, Williams & Wilkins, 2000).

The conjugates of the invention may be used to treat or prevent various diseases and disorders including lysosomal storage disorders listed in Table 2. One approach to treating these diseases is enzyme replacement therapy utilizing the conjugates. In some embodiments, the conjugates may be used to treat Fabry, Gaucher, Pompe or Niemann-Pick B disease.

Fabry disease is a rare, inherited lysosomal storage disorder with multisystemic effects. Patients with Fabry disease have a defect in the gene for the lysosomal enzyme α-galactosidase A (α-gal), also known as ceramide trihexosidase. This defect results in an inability or diminished ability to catabolize lipids with terminal α-galactosyl residues. In the absence of sufficient α-gal, these lipids, particularly globotriaosylceramide (GL-3; also known as Gb3, ceramide trihexoside, and CTH), accumulate progressively in the lysosomes of many cell types throughout the body. GL-3 accumulation in renal endothelial cells may play a role in renal failure.

Gaucher disease is an inherited lysosomal storage disorder. In Gaucher disease, a deficiency of the enzyme acid β-glucosidase (glucocerebrosidase) leads to the accumulation of the lipid glucocerebroside within the lysosomes of the monocyte-macrophage system. Lipid-engorged cells with eccentric nuclei, known as Gaucher cells, accumulate and displace healthy normal cells in bone marrow and visceral organs, causing a host of signs, including skeletal deterioration, anemia, hepatosplenomegaly, and organ dysfunction. In rare cases Gaucher cells affect the brain and nervous system.

Pompe disease is a debilitating, progressive and often fatal lysosomal storage disorder. People born with Pompe disease have an inherited deficiency of acid α-glucosidase. Acid α-glucosidase assists in the breakdown of glycogen, a complex sugar molecule stored within the lysosome. In Pompe disease, acid α-glucosidase activity may be dramatically reduced, dysfunctional, or non-existent, resulting in an excessive accumulation of glycogen in the lysosome. Eventually, the lysosome may become so clogged with glycogen that normal cellular function is disrupted and muscle function is impaired. Although there is glycogen storage in the cells of multiple tissues, heart and skeletal muscles are usually the most seriously affected. Patients typically experience progressive muscle weakness and breathing difficulty, but the rate of disease progression can vary widely depending on the age of onset and the extent of organ involvement.

Niemann-Pick B disease is a lysosomal storage disorder caused by mutations in the gene that encodes a lysosomal enzyme called acid sphingomyelinase (ASM). Due to these mutations, the ASM enzyme is not present in sufficient quantities to metabolize fat-like substances. In patients with Niemann-Pick B disease, fat-like substances, such as sphingomyelin and cholesterol, accumulate in body tissues and organs, resulting in their malfunction. Clinical manifestations of the disease are expressed in tissues such as spleen, liver, and lung, and to a lesser extent in bone marrow and lymph nodes.

Conjugates of the invention may be administered via any route of delivery including parenteral (e.g., subcutaneous, intravenous, intramedullary, intraarticular, intramuscular, or intraperitoneal), transdermal, and oral (e.g., in capsules, suspensions, or tablets). The conjugates may also be administered by direct administration to the nervous system (e.g. direct injection into the brain, intraventricularly, intrathecally). More than one route can be used concurrently, if desired.

Conjugates of the present invention may be administered alone or in conjunction with other agents, such as antihistamines or immunosuppressants. The term "in conjunction with" indicates that that the agent is administered at about the same time as the conjugate. The agent can be administered contemporaneously or it can be administered within a short time frame (e.g. within 24 hours) of administration of the conjugate.

A therapeutically effective amount of the conjugates of the invention may be administered at regular intervals depending on the nature and extent of the disease's effect. A therapeutically effective amount is a dosage amount that when administered at regular intervals is sufficient to treat the disease such as by ameliorating the symptoms associated with the disease, preventing or delaying the onset of the disease and/or lessening the severity or frequency of symptoms of the disease. Effective doses can be extrapolated from dose response curves derived from in vitro and in vivo data. The amount which will be therapeutically effective in the treatment of the disease will depend on the nature and extent of the disease effects and can also be determined by standard clinical techniques. The appropriate therapeutically effective dose will depend on the route of administration and the seriousness of the disease and should be decided by a treating clinician based on each patient's circumstances. The effective doses can be varied (e.g. increased or decrease) over time, depending on the needs of the individual.

Most commonly, proteinaceous compounds are administered in an outpatient setting at regular intervals depending on the nature and extent of disease. Administration at a "regular interval" as used herein, indicates that the therapeutically effective dose is administered periodocially. The interval an be determined by standard clinical techniques. For example, the conjugate is administered daily, weekly, biweekly, monthly, bi-monthly, or at longer intervals. The administration for a single individual need not be a fixed interval but can varied over time, depending on the needs of the individual.

EXAMPLES

Example 1

Preparation of a Dihydrazide PEG Conjugate of α-Galactosidase

One milligram of recombinant human α-galactosidase A (α-Gal) in 50 mM sodium phosphate pH 7 was treated overnight with 20 mU/mg Arthrobacter™ neuraminidase. A portion (0.5 mg) of the product in. 100 μL was incubated with 100 μL 10% w/v 10 kDa dihydrazide PEG (Sunbio) and 25 μL 0.2 M sodium succinate pH 5.5 (final pH ~5.8) overnight at 37° C. with 9 μL of 1 mg/mL recombinant *Dactylium dendroides* galactose oxidase. The product was dialyzed against 10 mM sodium phosphate pH 7 and applied to a DEAE Sepharose™ column (Pharmacia) equilibrated with the same buffer and eluted with a gradient from 0 to 0.5 M NaCl in 10 mM phosphate pH 7. The peak fraction was concentrated and exchanged into 0.05 M sodium phosphate pH 7 using 50 kDa MWCO centrifugal ultrafilters (Amicon). A portion was run on a 4-12% SDS polyacrylamide gel (NuPAGE™, Invitrogen) using a neutral-pH MOPS/SDS running buffer at 200 V for 1 hour, and the gel stained with Coomassie™ blue. This demonstrated approximately equal amounts of mono- and di-PEGylated products as assessed by gel mobility.

Example 2 pH Dependence of Hydrazide PEG Conjugate Stability

Figure 5:
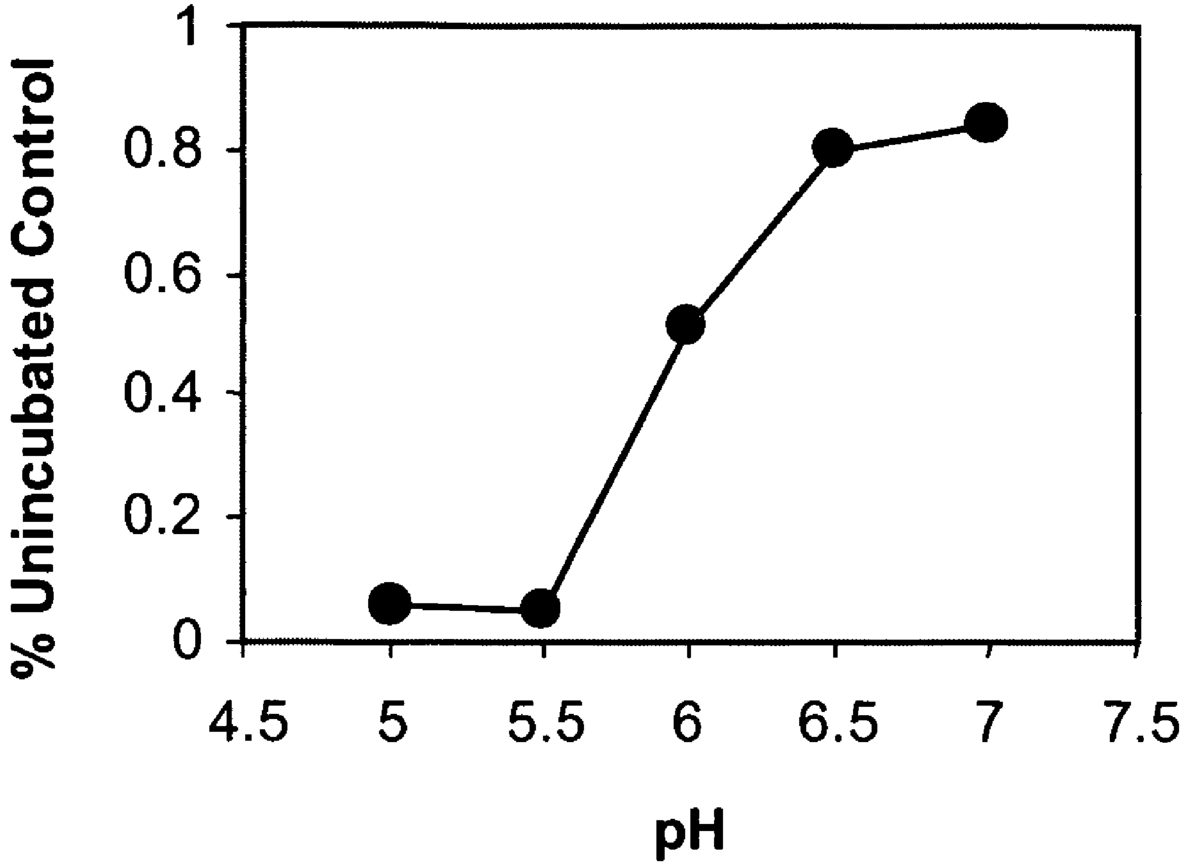
FIG. 5 shows the pH-dependent dissociation of a pendant hydrazide PEG conjugate with α-galactosidase A. A pendant hydrazide PEG bearing on average eight propionic acid hydrazide groups was conjugated with galactose-oxidized α-galactosidase as described for FIG. 1. The conjugate was purified by anion exchange chromatography and exchanged into buffers of varying pH and incubated overnight at 37° C. as described in Example 2. The amount of protein in PEGylated form relative to an unincubated control was determined by densitometry of the Coomassie-stained gel following SDS-PAGE.

Aliquots (4 μL, ~2 μg) of a DEAE Sepharose™ purified dihydrazide conjugate prepared as described in Example 1 were incubated overnight in 45 μL 50 mM buffer (either phosphate, succinate, citrate, or acetate) at between pH 7.0 and 5.0 for 14 hours at 37° C., and then concentrated on Microcon™ 50 centrifugal ultrafilters (Amicon) for 10 minutes at 4° C. The retained volumes were collected and a portion of each run on a SDS polyacrylamide gel (NuPAGE™, Invitrogen) as described in Example 1. As shown in FIG. 5, incubation at pH 7 resulted in retention of more than 80% of the PEGylated material in PEGylated form (as compared to an unincubated control), while reducing the pH of the solution led to a decrease in the amount of PEGylated material. At pH 5.5, less than 10% of the initial PEGylated material remained. There was a corresponding increase in the free α-galactosidase.

Example 3

Effect of PEGylation on Binding of αGal to CIMPR In vitro

Figure 6:
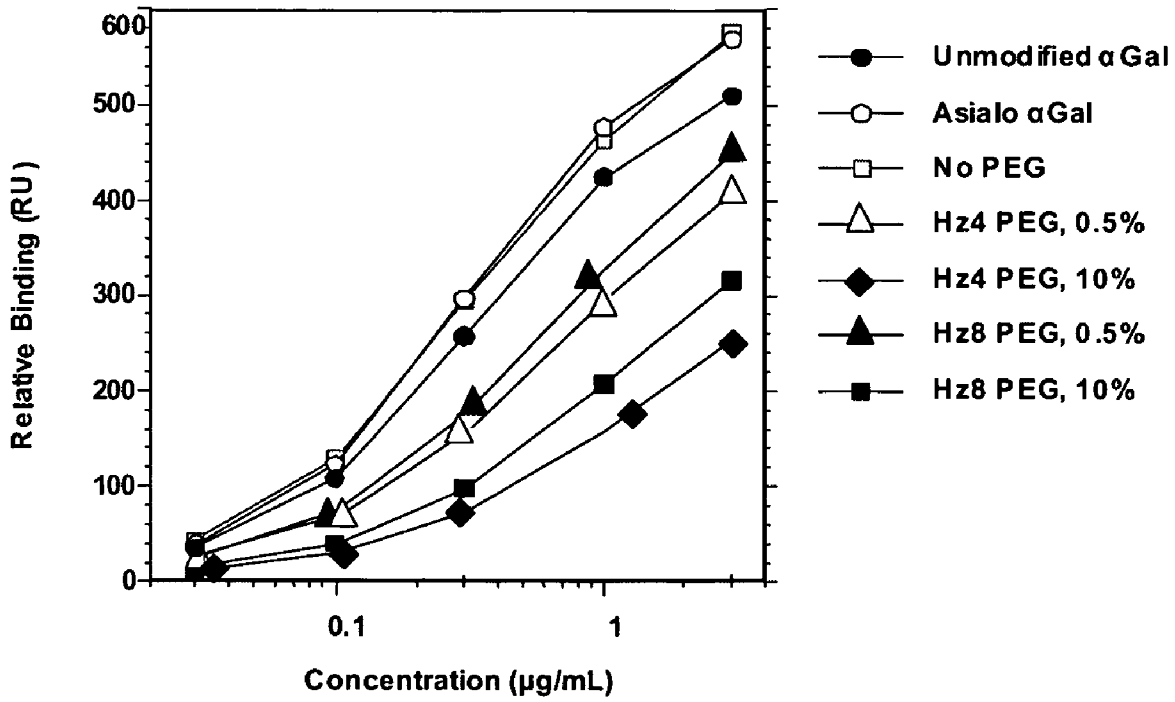
FIG. 6 shows results of a BIAcore™ analysis for the interaction of PEG-glycoprotein conjugates with the cation independent mannose-6-phosphate receptor (CIMPR). The extent of unmodified α-galactosidase or galactosidase conjugate binding to CIMPR (in RU) was determined using immobilized soluble CIMPR on a dextran-coated chip. Two hydrazide PEGs (10 kDa MW, SunBio) were used for preparing the conjugates by the scheme shown in FIG. 1: (1) a 4-arm star-type PEG (dendrimer; Hz4PEG) and (2) an 8-arm pendant PEG (Hz8PEG). Both were functionalized with hydrazide groups either at the PEG termini (Hz4PEG) or internally by random co-polymerization (Hz8PEG). This shows 10-fold higher concentrations of the Hz4-PEG conjugate were required to obtain the same degree of receptor binding as obtained with unmodified α-galactosidase.

Two preparations of α-galactosidase conjugated to either a 4-arm dendrimer ("star") hydrazide PEG (Hz4PEG) or a 8-arm hydrazide PEG (Hz8PEG), each of 10 kDa molecular weight, in which propionyl hydrazide groups were incorporated into the PEG main chain at random positions (SunBio) were prepared as described in Example 1, except that concentration of PEGs in the conjugation step was either 0.5 or 10% w/v. The purified conjugates were assessed for binding to purified cation-independent mannose-6-phosphate receptor (CIMPR) by surface plasmon resonance (Biacore). Conjugate or unmodified α-galactosidase were diluted and pumped tangentially across a Biacore flow cell at 20 μL/min. The soluble form of CIMPR (lacking the membrane anchor sequence) was conjugated to an activated dextran-coated surface on the optical face of the cell using NHS chemistry. Binding (assessed by a change in refractive index) expressed in RU (resonance units), less the RU generated by a control cell lacking receptor exposed to the same solution after 3 minutes was plotted against the concentration of conjugate. The data (FIG. 6) show that maximum inhibition of binding to receptor was obtained by prior conjugation of the enzyme with 10% w/v 4-arm (Hz4)PEG. Approximately 10-fold higher concentration of PEG conjugate was required to produce the same change in RU as unmodified α-galactosidase.

Example 4

In vivo Uptake of HzPEG/□-Galactosidase Conjugate in Fabry Mice

Figure 7:
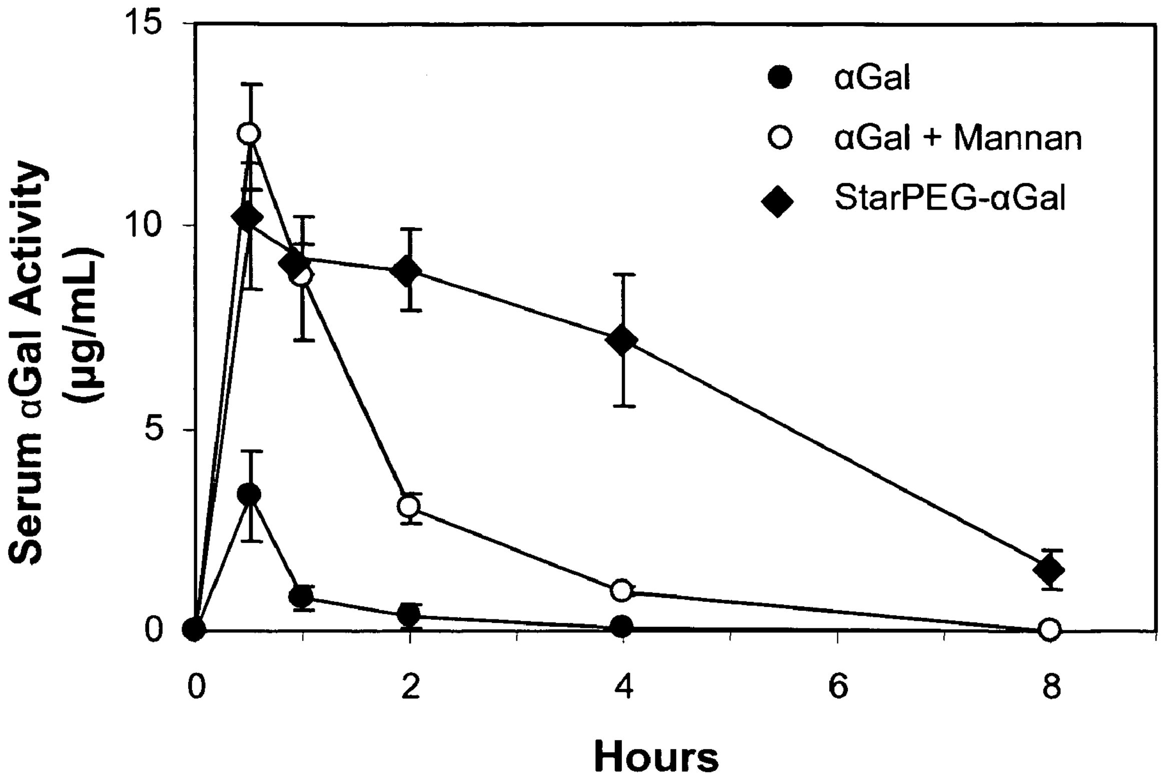
FIG. 7 shows results of a pharmacokinetics study with intravenously administered α-galactosidase and a PEG-α-galactosidase conjugate in Fabry mice. An initial blood sample was drawn prior to protein injection (plotted as zero time). Proteins were injected at 1 mg/kg body weight by tail vein and blood withdrawn at 0.5, 1, 2, 4, and 8 hours. Serum was prepared and assayed for galactosidase activity using a 4MU substrate as described in Example 4.

A conjugate of α-galactosidase A with a 6-arm star hydrazide PEG (20 kDa, SunBio) prepared in a similar fashion as described in Example 1 was injected at 1 mg/kg body weight into the tail vein of 4-month-old α-galactosidase knockout mice, and blood samples (~100 μL) withdrawn at various intervals. Separate sets of mice were either injected with unmodified α-galactosidase or enzyme co-injected with 100 mg/kg yeast mannan (Sigma) to transiently block uptake by mannose receptor. Serum was prepared and the amount of enzyme remaining in circulation determined by dilution and assay using 4-methylumbelliferyl-α-D-galactoside (4MU-D-αGal, Sigma) as a substrate in the presence of 0.12 M N-acetylgalactosamine to suppress α-galactosidase B activity (Mayes et al., Clin. Chim. Acta (1981) 112:247-251) as shown in FIG. 7. Mannan co-injection resulted in a two-fold increase in the area under the concentration-time curve whereas PEG conjugation resulted in a six-fold increase. The half-life of the longer-lived PEG conjugate in circulation was approximately 4 hours.

Figure 8:
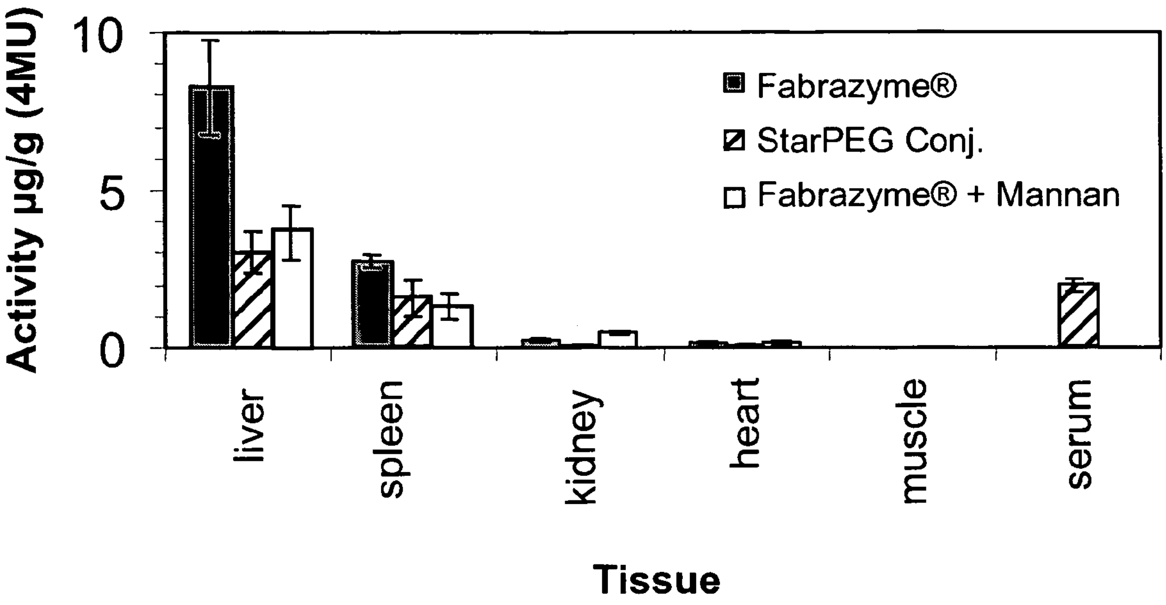
FIG. 8 shows biodistribution of α-galactosidase (Fabrazyme®) or PEG-Fabrazyme® conjugate in Fabry mice. Proteins were injected at 1 mg/kg body weight and the organs harvested 8 hours after injection. Galactosidase activity was determined using a 4MU substrate as described in Example 4.
Figure 9:
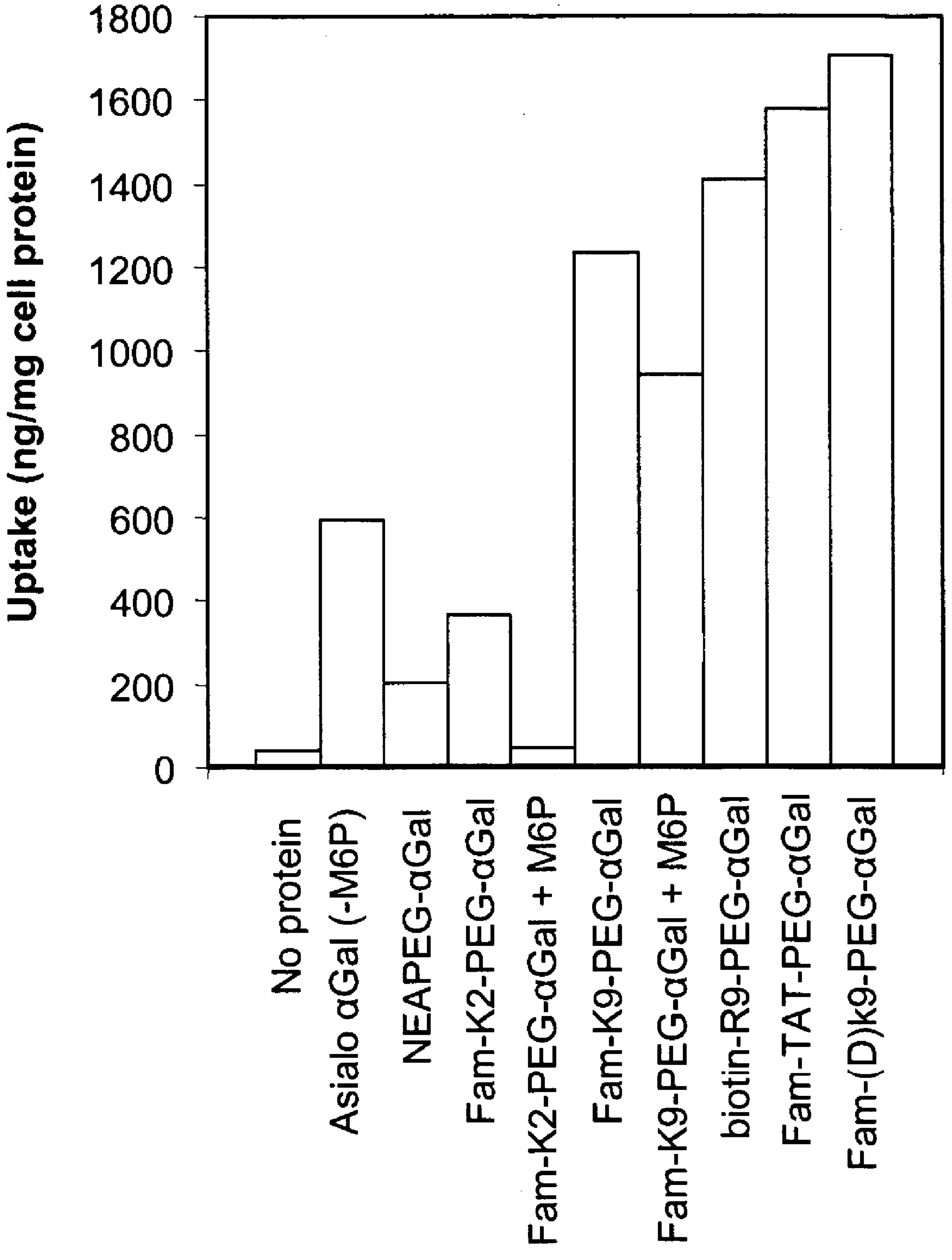
FIG. 9 is intracellular uptake levels of various peptide-PEG-α-galactosidase conjugates. NEA-PEG conjugates prepared as described in Example 7 were coupled with various peptides (SEQ ID NOs:2-6) as described, and incubated with murine fibroblasts expressing the cation-independent mannose-6-phosphate (M6P) receptor overnight. In two cases, 2 mM free M6P was added to the culture medium with peptide conjugates ("+M6P").

Mice in the same experiment were sacrificed after 8 hours and biodistribution of the conjugates was determined by enzymatic assay on 10% w/v homogenates of the tissues prepared in 0.15% Triton™ X-100, 14.5 mM citric acid, 30 mM sodium phosphate pH 4.4 using 4MU-D-αGal as substrate. The activities in the homogenates were normalized to protein content determined by BCA assay (Pierce). The data shown in FIG. 8 show a significant reduction in the uptake in liver by the PEG conjugate. Even after 8 hours, a significant amount of the recovered activity was still present in serum.

A portion of the liver was fixed in 4% neutral-buffered formalin overnight at 4° C., embedded in paraffin, and sectioned. Paraffin was removed from the mounted sections, which were stained using a monoclonal antibody against the human α-galactosidase at 2.5 μg/mL, and visualized by a goat anti-mouse horseradish peroxidase secondary antibody using diaminobenzidine as substrate. The sections were counterstained with Mayers Hematoxylin. Whereas the unmodified control enzyme showed strong staining of Kupffer cells with some staining of hepatocytes, staining of Kupffer cells was substantially reduced with the PEGylated enzyme, while hepatocytes stained to a similar extent.

Example 5

Preparation of an αGal Conjugate With A Heterobifunctional PEG

A precursor (BTNEA) was obtained by reaction of 27 mg nipsylethylamine (NEA), 76 mg EDC, 40 mg N-hydroxysuccinimide and 37.4 mg t-BOC-threonine in 93% DMSO with 35 mM imidazole pH6 overnight at 50° C. The product was purified by reverse-phase chromatography on a C18 column (Higgins Targa), eluting with 0.1% TFA (10 min) followed by a gradient of 0-50% acetonitrile (1%/min) in 0.1% trifluoroacetic acid (TFA). The product eluting at 46 minutes was collected and taken to dryness. The product showed absorbance peaks similar to NEA (270,353 nm cf. 268,345 nm for NEA), which shifted upon reduction with TCEP (258,308 nm cf. 256,312 nm for NEA). The product, dissolved in 100 μL DMSO, was deblocked by addition of 24 μL TFA, and incubated at 50° C. for 15 hours, and purified by C18 reverse phase chromatography under the same conditions (retention time 26 min). The peak was collected and taken to dryness and then dissolved in DMSO. The deblocked material was oxidized by reaction with 25 mM $NaIO_4$ in 50% DMSO-buffered with 0.05 M HEPES pH 7.4 for 15 minutes at room temperature, followed by C18 chromatography (product GNEA eluting at 31.8 min).

An 8-arm 20 kDa MW hydrazide pendant PEG (SunBio, 1.5 mmol) in which propionic acid hydrazide groups were randomly inserted, was reacted with 1.6 μmol GNEA in 50% DMSO, 0.025 M succinate pH 5.6 (total 0.42 mL) overnight at 37° C. The reaction was diluted to 0.8 mL with cold 10 mM sodium phosphate pH 7, and dialyzed against the same buffer and then against water. The product was recovered, lyophilized, and the NEA content determined by reduction and absorbance at 346 nm (1.05 mol:mol PEG).

Neuraminidase-treated αGal (0.23 mg) was reacted with 10% GNEA-PEG in 50 mM succinate pH 5.5 in the presence of 7.5 μg recombinant galactose oxidase overnight at 37° C. The product was diluted with 10 mL of 10 mM sodium phosphate pH 7 and purified over a column of DEAE Sepharose™ as in Example 1.

A portion of purified GNEA PEG conjugate (25 μg) was reacted with 4.25 nmol of fluoresceinated peptides of SEQ ID NO:2 or SEQ ID NO:3 overnight at 4° C. and purified away from unreacted free peptide by elutriation on centrifugal ultrafilters (Centricon™ 50, Amicon™ Corp). The final products contained 2.1 and 1.6 peptides per conjugate (SEQ ID NO:2 and SEQ ID NO:3, respectively) as determined from the absorbances at 495 nm and 280 nm. A cell uptake experiment such as described in Example 8 showed no significant increase in lysate activity after overnight incubation with the conjugate prepared with the peptide of SEQ ID NO:2 in the medium. In contrast, incubation with comparable amounts of neuraminidase-treated αGal produced over 10-fold increase in the activity of the αGal activity in the lysate.

Example 6

Preparation of Thiol-Reactive PEG

A 16-arm PEG in which pendant propionic acid groups are introduced by copolymerization (SunBio, 5.25 μmol) was reacted with 126 μmol nipsylethylamine (NEA), 420 μmol N-(3-dimethylaminopropyl)-N'-ethylcarbodiimide (EDC), 168 μmol N-hydroxysuccinimide, in 1.6 mL 50% dimethylsulfoxide, 0.1 M imidazole pH 6 overnight at 50° C., yielding a two-phase mixture. Additional 0.1 M imidazole (1.5 mL) was added and the mixture incubated an additional 3 hours at 50° C. The product was purified by extensive dialysis against water. The NEA content of the PEG, determined by the absorbance at 350 nm, was 9.3 NEA/PEG. A small fraction (<10%) of the PEG prepared in this manner was bound by DEAE-Separose™ in 10 mM sodium phosphate pH7 buffer. This component was removed from the NEAPEG by passage over DEAE Sepharose™ prior to use in conjugation reactions.

Example 7

Peptide-PEG Conjugates of □Gal Using Hydrazide/Thiol Chemistry

An aliquot of α-galactosidase (1.16 mg in 0.25 mL of 50 mM sodium phosphate pH 7) was treated with 20 mU/mg Arthrobacter™ neuramimidase overnight at 37° C. The product was then combined with 0.125 mL 0.2 M succinate (pH 5.4), 46.5 μg recombinant *Dactylium* galactose oxidase, and 0.05 mL 50 mM 3-(2-pyridyldithio)propionyl hydrazide (PDPH, Pierce) in a final volume of 0.5 mL, and incubated overnight at 37° C. The product was then dialyzed overnight against cold 50 mM sodium phosphate pH 7. The product (2.3 mg/mL) was reacted with 10 mM tris-carboxyethylphosphine (TCEP, Pierce) to expose the thiols from the conjugated PDPH for 10 minutes at room temperature followed by 3 rounds of desalting on 50 kDa MWCO centrifugal ultrafilters (Centricon™, Amicon™) with cold degassed buffer. The product was then reacted with 1% (w/v) of a thiol-reactive 16-arm pendant NEA-PEG prepared as described in Example 6 in the same buffer overnight at 4° C. The reaction was dialyzed against 10 mM sodium phosphate pH 7, loaded on an DEAE Sepharose™ column equilibrated with the same buffer, and eluted with 0.25 M NaCl in 50 mM phosphate pH 7. The eluate was exchanged into 50 mM sodium phosphate pH 7 on centrifugal ultrafilters. Aliquots (20 μg protein each) were reacted with FAM- or biotin-labeled peptides (SEQ ID NO:1, SEQ ID NO:2, SEQ ID NO:3, SEQ ID NO:4, SEQ ID NO:5, AND SEQ ID NO:6) (3.75 nmol each) overnight in 50 mM sodium phosphate pH 7 and a final volume of 50 μL and purified by desalting on 50 kDa MWCO centrifugal ultrafilters using the same buffer. The products showed 38-56% of the specific activity of the initial α-galactosidase. The conjugates prepared with fluoresceinated peptides contained between 1.8 and 8.5 peptides per protein. A diagrammatic representation of the process is shown in FIG. 4.

Example 8

Peptide-Mediated Cell Uptake of αGal Conjugates In Vitro

Peptide conjugates prepared in Example 7 (each 0.1 nmol/min activity using p-nitrophenyl-α-D-galactoside as substrate) were incubated with an immortalized wild-type murine fibroblast cell line (TME7, Munier-Lehmann et al., J. Biol. Chem. (1996) 271:15166-15174) in 24-well plates in 0.5 mL uptake medium (DMEM/F12 with 5% calf serum, 3% BSA and 25 mM HEPES pH 6.7) for 24 hrs in a 37° C. incubator with 5% $CO_2$. Some of the media were supplemented with 2 mM mannose-6-phosphate (M6P) to suppress uptake by the cation-independent M6P receptor, the major route of uptake of the unmodified enzyme by this cell line.

The cells were washed three times with PBS pH 6.5 and lysed with 0.5×PBS pH 6.5, 1% Triton™ X-100 with protease inhibitors (Roche), followed by brief sonication in an ice bath slurry. The activity in the lysates were determined as described in Example 4. Activities present in the lysates normalized to protein content as determined by BCA assay (Pierce) are shown in FIG. 3. The internalization of the enzyme was verified by staining cells exposed to conjugates under similar conditions using a substrate that produces an insoluble colored product (X-α-Gal). This showed strong staining in the cytoplasm but not in the nucleus of cells exposed to the R9 (SEQ ID NO:6), Tat (SEQ ID NO:2), and k9 (SEQ ID NO:5) peptide conjugates, indicating that the cell-associated activity was internalized and not bound to the surface of the cells.

Example 9

Use of Thioesters in the Preparation of Hydrazone-Linked Conjugates of Lysosomal Disease Glycoproteins One micromole of glutamic acid γ hydrazide is converted to the acetone ketal by incubation for 1 hour with 10 μmol acetone in DMSO at room temperature. Then 2 μmol N-succinimidyl-S-acetylthioacetate (SATA, Pierce Chemical Co.) is added and the incubation continued overnight at room temperature. The product, S-acetyl thioacetamide glutamic acid hydrazide (SATAGH), is purified by anion exchange chromatography on QAE Sephadex™ in 20 mM ammonium formate pH 7, eluting with a gradient to 0.5 M ammonium formate pH 7. The $A_{215}$ peak corresponding to the amide product is collected and lyophilized. The cargo glycoprotein is separately desialated by overnight digestion with 20 mU/mg Arthrobacter neuraminidase in 50 mM sodium citrate pH 6, and then treated with 10 μg/mg recombinant galactose oxidase overnight in the same buffer. To the oxidized glycoprotein, 5 mM SATAGH is added in 25 mM succinate pH 5.5 and the mixture incubated at room temperature for 3 hours. The hydrazone conjugate is purified by ultrafiltration on a Centricon™ YM-30 filter or dialysis against 25 mM EDTA, 25 mM phosphate pH 7.2. A 10-fold molar excess of a multiarm NEA-PEG is then added along with 0.2 M hydroxylamine to deprotect the thiol, and the mixture incubated overnight at room temperature to generate the disulfide-linked PEG adduct.

Example 10

Use of Pyridyl Hydrazides to Generate Polysialic Acid Conjugate of α-Galactosidase One gram of polysialic acid PSA (colominic acid, 30 kDa avg. MW) is dissolved at 100 mg/ml in 0.1 N NaOH and deacylated by incubation at 37° C. for 4 hours. The product is neutralized by the addition of acetic acid to 0.1 M, and the mixture extracted with chloroform:methanol (3:1). Sodium acetate is added to the aqueous phase (to 0.2 M), and the PSA precipitated with 3 volumes of ethanol followed by high speed centrifugation (10,000 g for 20 min). The pellet is washed with 85% ethanol and taken to dryness in vacuo. The dried pellet is dissolved to 100 mg/ml with water. Separately, an adaptor containing a pyridyl hydrazine coupled to nipsylethylamine is generated by reaction of 100 μmol acetone-5-succinimidyloxycarbonyl)-pyridine-2-ylhydrazone (SANH) (EMD Biosciences) with 150 μmol nipsylethylamine overnight at room temperature in 1 mL DMSO. To 100 mg deacylated polysialic acid (~3.3 μmol) is added 10 μmol SANH-NEA product in 5 mL 0.1 M sodium acetate pH 5 and the mixture incubated overnight at room temperature to form the hydrazone. The product is dialyzed against PBS, then water, and then precipitated with ethanol as before. The pellet is washed with 85% ethanol, taken to dryness in vacuo, and finally re-dissolved to 100 mg/mL in water. This material is conjugated with a reduced PDPH conjugate of αGal prepared as described in Example 7. The product is purified from unconjugated PSA by diafiltration using a 50 kDa MWCO membrane, and exchanged into 50 mM sodium phosphate pH 7.

Example 11

Synthesis of a PEG-rhα-Gal Conjugate

Fabrazyme® (recombinant human α-galactosidase) was reacted at 5 mg/mL with a 25:1 molar excess of NHS dPEG™$_8$ SATA (Quanta Biodesign) for 2 hours at 25° C. in 50 mM Na phosphate pH 7. The reaction was quenched by a 100-fold molar excess of Tris HCl pH 7 for 30 minutes and the product purified by dialysis. This produced 4.8 protected (S-acetyl) thiol groups per 90 kDa homodimer, as determined by reduction in free lysine content of the enzyme by assay with trinitrobenzenesulfonic acid (TNBSA, Pierce). The conjugate was then incubated in 50 mM hydroxylamine hydrochloride, 2.5 mM EDTA, 50 mM Na phosphate pH 7.2 in the presence of a 30-fold molar excess of a 6-arm (star) 20 kDa NEA-PEG prepared as in example 6, except substituting a 6-arm star 20 kDa carboxylic acid-terminated PEG (SunBio) as the starting material for the pendant 16-arm PEG described in example 6. After two hours at 25° C., the reaction was buffer exchanged into 50 mM Na phosphate pH7, 2.5 mM EDTA and incubated overnight at 25° C. The product was 100% in PEGylated form by SDS PAGE. The product was purified by anion exchange chromatography on DEAE Sepharose, applying the reaction product in 10 mM Na phosphate pH 7, washing with the same buffer, and eluting with 0.25 M Na phosphate pH 7. The product was then dialyzed into 50 mM Na phosphate pH 7.

A SATA-dPEG$_4$-conjugate of diphtheria toxin $CRM_{197}$ was separately generated by reaction of a 10-fold molar excess of NHS SATA-dPEG$_4$-NHS (Quanta Biodesign) with CRM197 (List Biological Laboratories) in 10 mM Na phosphate pH 7.4 for 2 hours at 25° C., and purified by ultrafiltration against the same buffer. A 2-fold molar excess of the SATA-dPEG$_4$-$CRM_{197}$ conjugate was then incubated with the Star-NEA-PEG-α-Gal conjugate in 50 mM hydroxylamine hydrochloride, 2.5 mM EDTA, 50 mM Na phosphate pH 7.2 for 2 hours at 25° C. to deprotect the linker-introduced thiols on the $CRM_{197}$. The mixture was then buffer exchanged into 2.5 mM EDTA, 50 mM Na phosphate p H7 and incubated overnight at 25° C. in the same buffer to complete the coupling reaction. The product was purified by size-exclusion chromatography on Superdex 200 resin in 50 mM Na phosphate pH 7. The PEGylated product eluted as a single HMW peak which had no free acid galactosidase or $CRM_{197}$. Upon reduction, SDS PAGE analysis showed the presence of $CRM_{197}$ to acid galactosidase subunits in approximately 1:1 ratio.

Example 12

Vero Cell Uptake of CRM PEG-α-Gal Conjugate

The CRM conjugate prepared as in example 11 or the star PEG-α-Gal conjugate without CRM is added (5 μg/mL) to separate aliquots 0.5 mL uptake medium (Vero cell growth medium buffered with 10 mM HEPES pH 6.7) and applied to Vero cells. To block uptake mediated by the cation-independent mannose-6-phosphate (M6P) receptor, 2 mM M6P is added to the medium in some wells. In additional control wells, free $CRM_{197}$ is added at a 10-fold excess over the conjugate, and other wells receive no conjugate to assess the endogenous level of α-galactosidase activity. The plate is placed in an incubator overnight at 37° C., 5% $CO_2$. The cell layers are washed 3 times with 1 mL PBS and lysed with ½×PBS pH 6.5, 1% Triton X-100, 1× protease inhibitor cocktail ("Complete", Roche). The lysates are then assayed for acid α-galactosidase activity using 4-MU-α-galactoside substrate (Sigma) normalized to total protein content obtained by BCA assay (Pierce). The activity in the control wells receiving no protein (endogenous activity) is subtracted from the activity in the wells which received protein to determine uptake. The extent of masking is determined from the amount of uptake which is sensitive to M6P in the medium without and with PEGylation and/or CRM conjugation. CRM dependent uptake is determined from the α-galactosidase uptake observed in the wells containing the CRM conjugate less the amount of uptake observed in wells containing excess CRM.

All publications and patents cited in this disclosure are incorporated by reference in their entirety. To the extent the material incorporated by reference contradicts to or is inconsistent with this disclosure, the instant disclosure supersedes. All examples are provided for illustration only and are nonlimiting. Further, all numbers expressing reaction parameters are approximate, unless expressly indicated or the context requires otherwise.

The invention claimed is:

1. A conjugate comprising:

(1) a therapeutic glycoprotein (G), (2) a masking moiety (M) covalently linked to an amino acid residue of the glycoprotein through a first linker ($L^1$), and (3) a targeting moiety (T) covalently linked to the masking moiety through a second linker ($L^2$), wherein:

the conjugate has formula $G(L^1\text{-}M(L^2\text{-}T)_n)_m$ wherein $2 \leqq m \leqq 16$, and n <1 or $1<n \leqq 20$, the therapeutic glycoprotein is α-galactosidase A, the masking moiety is polysialic acid (PSA), and $L^1$ and $L^2$ each comprise a disulfide, and wherein the glycoprotein is released from the conjugate under lysosomal conditions.

2. The conjugate of claim 1, wherein the amino acid residue is a lysine residue.

3. The conjugate of claim 1, wherein the masking moiety is degradable under the lysosomal conditions thereby allowing the release of the glycoprotein.

4. The conjugate of claim 1, wherein the targeting moiety is a non-endogenous protein, a receptor-binding peptide, an antibody to a receptor, or a natural receptor ligand.

5. The conjugate of claim 1, wherein at least one of the linkers $L^1$ and $L^2$ comprises a formula selected from:

(XIX)

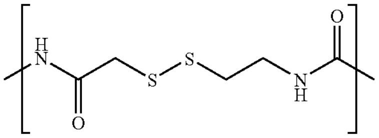

and (XX)

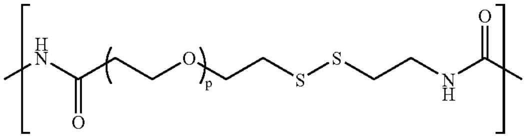

wherein $2 \leq p \leq 12$, and wherein any one or more of the terminal atoms of formulas XIX and XX may be derived from the element G, M, or T to which the formula is attached.

6. A pharmaceutical composition, comprising the conjugate of claim 1 and a pharmaceutically acceptable excipient.

7. The conjugate of claim 1, wherein at least one of the linkers $L^1$ and $L^2$ comprises the formula

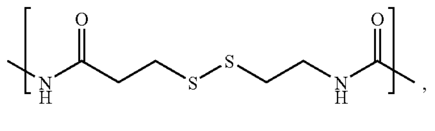

wherein either or both of the terminal atoms of the formula may be derived from the element G, M, or T to which the atoms are attached.

8. The conjugate of claim 1, wherein $n<1$.

9. The conjugate of claim 1, wherein $1<n \leq 20$.

10. The conjugate of claim 1 wherein the conjugate comprises a formula selected from:

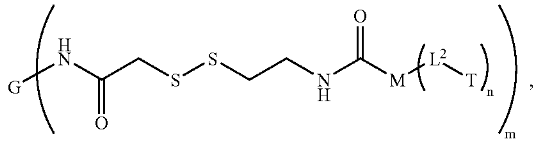

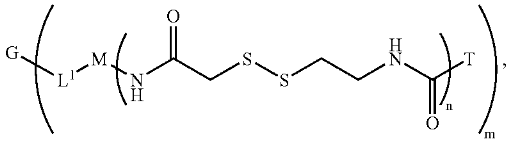

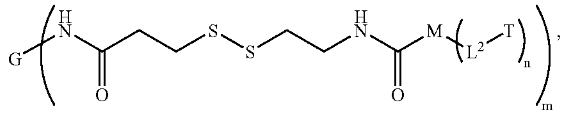

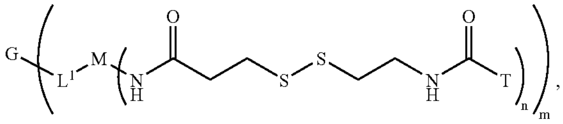

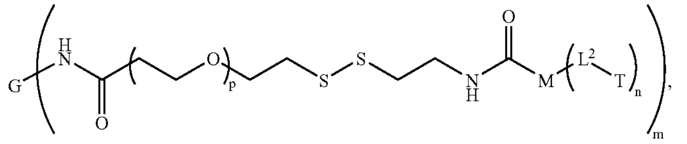

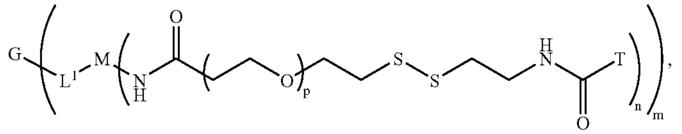

(XXXI)

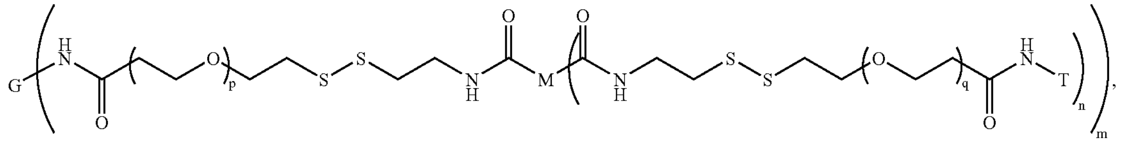

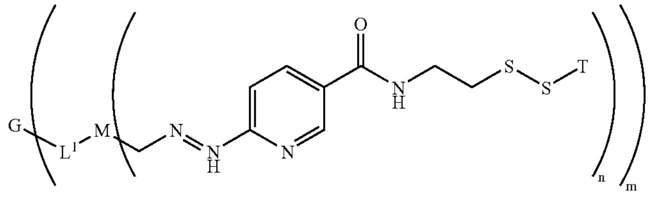

, and

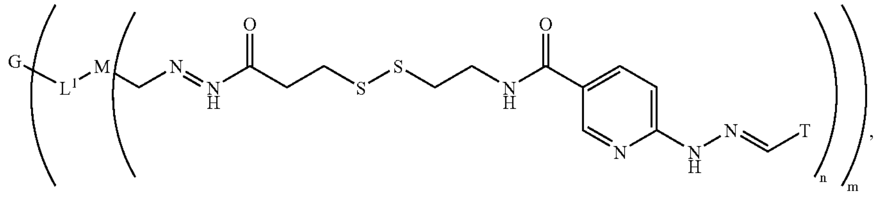

wherein any one or more of the terminal atoms of the formulas between elements G and M and between elements M and T may be derived from the element to which the atoms are attached.

11. The conjugate of claim 1 wherein at least one of the linkers $L^1$ and $L^2$ comprises a formula selected from:

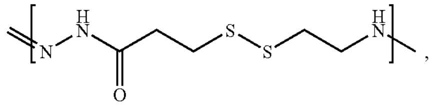

-continued

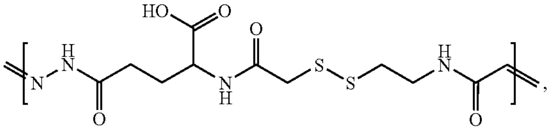

,

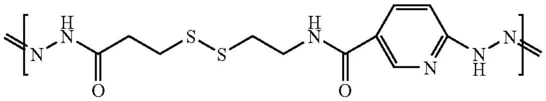

,

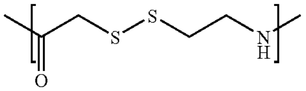

,

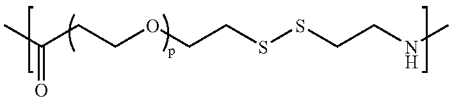

, and

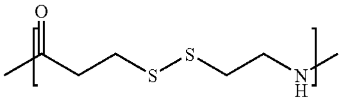

.

12. The conjugate of claim 1, wherein the PSA comprises 2-10 functional groups for conjugation to the glycoprotein and the targeting moiety.

13. The conjugate of claim 1, wherein $L^1$ further comprises the formula

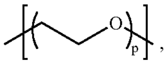

, wherein $2 \leqq p \leqq 12$, and $L^2$ further comprises the formula

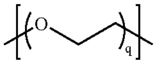

, wherein $2 \leqq q \leqq 12$.

14. The conjugate of claim 10, comprising the formula:

(XXXI)

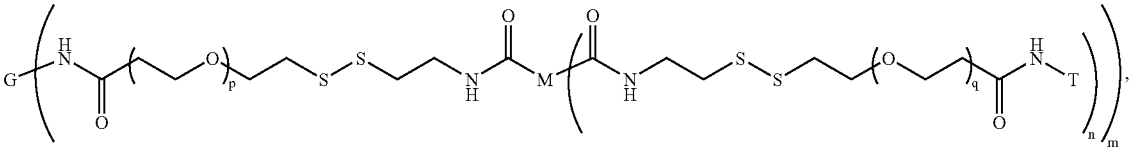

, wherein $2 \leqq p \leqq 12$ and $2 \leqq q \leqq 12$, independently of each other, and wherein any one or more of the terminal atoms of the formula between elements G and M and between elements M and T may be derived from the element to which the atoms are attached.

15. The conjugate of claim 12, wherein the PSA comprises 3, 4, or 5 functional groups for conjugation to the glycoprotein and the targeting moiety.

16. A conjugate comprising:

(1) a therapeutic glycoprotein (G), (2) a masking moiety (M) covalently linked to an amino acid residue of the glycoprotein through a first linker ($L^1$), and (3) a targeting moiety (T), comprising covalently linked to the masking moiety through a second linker ($L^2$), wherein:

the conjugate has formula $G(L^1\text{-}M(L^2\text{-}T)_n)_m$, wherein $2 \leqq m \leqq 16$, and n <1 or $1 < n \leqq 20$, the therapeutic glycoprotein is α-galactosidase A, the masking moiety is polysialic acid (PSA), $L^1$ and $L^2$ each comprise a disulfide, and the targeting moiety comprises the amino acid sequence of SEQ ID NO:1, SEQ ID NO:2, SEQ ID NO:3, SEQ ID NO:4, SEQ ID NO:5, or SEQ ID NO:6, and wherein the glycoprotein is released from the conjugate under lysosomal conditions.

17. The conjugate of claim 1, wherein at least one of the linkers $L^1$ and $L^2$ further comprises a formula selected from:

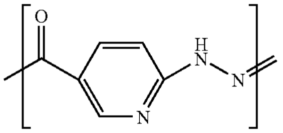

,

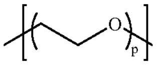

,

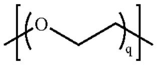

,

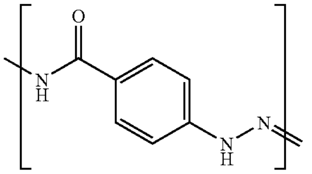

, and

-continued

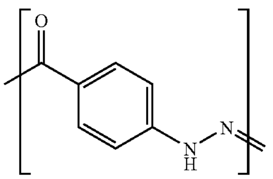

.

18. The conjugate of claim 1 wherein the disulfide of $L^1$, $L^2$, or both is formed with the terminal sulfur atom of a formula selected from:
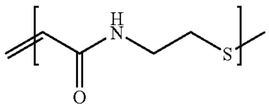
,
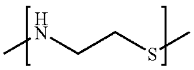
, and
-continued
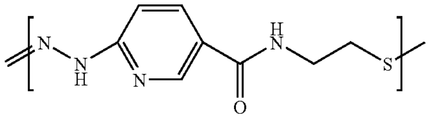
,
and a sulfur atom of G, M, or T.
* * * * *

UNITED STATES PATENT AND TRADEMARK OFFICE

CERTIFICATE OF CORRECTION

PATENT NO. : 7,341,720 B2

APPLICATION NO. : 11/398949

DATED : March 11, 2008

INVENTOR(S) : James Stefano

It is certified that error appears in the above-identified patent and that said Letters Patent is hereby corrected as shown below:

IN THE CLAIMS

In claim 10, column 36, line 35, replace the following formula:

“ 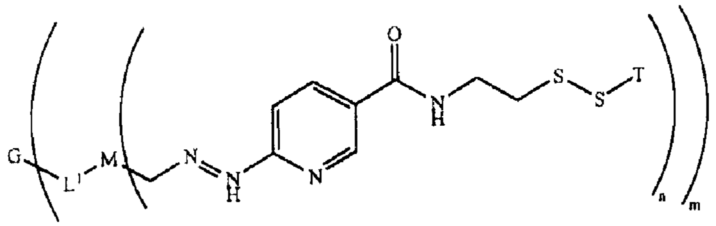 ”

with:

-- 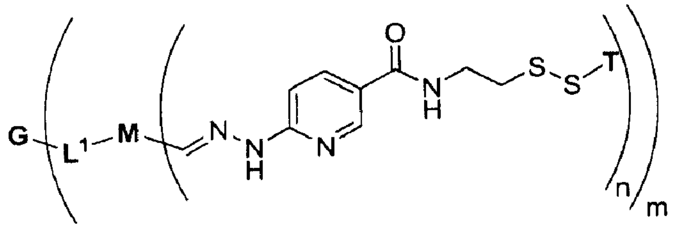 --.

UNITED STATES PATENT AND TRADEMARK OFFICE

CERTIFICATE OF CORRECTION

PATENT NO. : 7,341,720 B2
APPLICATION NO. : 11/398949
DATED : March 11, 2008
INVENTOR(S) : James Stefano It is certified that error appears in the above-identified patent and that said Letters Patent is hereby corrected as shown below:

In claim 10, column 36, line 42, replace the following formula:

"
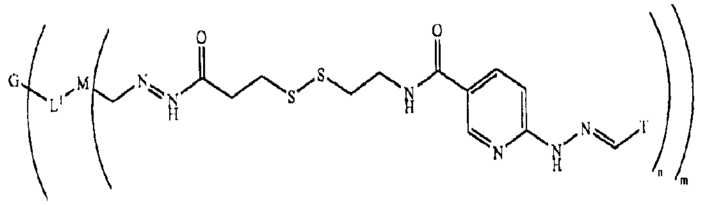
"

with:

--
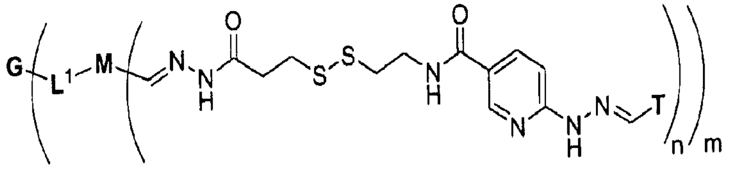
--.

Signed and Sealed this

Eighth Day of July, 2008

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: AMIDATION

<400> SEQUENCE: 1

Gly Lys Lys Lys Lys Lys Lys Lys Lys Lys Gly Cys
1               5                   10


<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: May be fluorescein conjugated
<220> FEATURE:
<221> NAME/KEY: MOD_RES
<222> LOCATION: (18)
<223> OTHER INFORMATION: AMIDATION

<400> SEQUENCE: 2

Gly Gly Gly Tyr Gly Arg Lys Lys Gly Gly Gln Arg Arg Arg Gly Gly
1               5                   10                  15

Gly Cys


<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: May be fluorescein conjugated
```

-continued

```
<220> FEATURE:
<221> NAME/KEY: MOD_RES
<222> LOCATION: (16)
<223> OTHER INFORMATION: AMIDATION

<400> SEQUENCE: 3

Gly Gly Gly Gly Gly Lys Gly Gly Gly Lys Gly Gly Gly Gly Gly Cys
1               5                   10                  15


<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: May be fluorescein conjugated
<220> FEATURE:
<221> NAME/KEY: MOD_RES
<222> LOCATION: (16)
<223> OTHER INFORMATION: AMIDATION

<400> SEQUENCE: 4

Gly Gly Gly Lys Lys Lys Lys Lys Lys Lys Lys Lys Gly Gly Gly Cys
1               5                   10                  15


<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: May be fluorescein conjugated
<220> FEATURE:
<221> NAME/KEY: MOD_RES
<222> LOCATION: (4)..(12)
<223> OTHER INFORMATION: D-Lys

<400> SEQUENCE: 5

Gly Gly Gly Lys Lys Lys Lys Lys Lys Lys Lys Lys Gly Gly Gly
1               5                   10                  15


<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: May be biotin conjugated

<400> SEQUENCE: 6

Gly Arg Arg Arg Arg Arg Arg Arg Arg Arg Gly Cys
1               5                   10


<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
```

-continued

```
      peptide

<400> SEQUENCE: 7

Thr His Arg Pro Pro Met Trp Ser Pro Val Trp Pro
1               5                   10


<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ser Ser Leu Asn Ile Ala
1               5


<210> SEQ ID NO 9
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Cys Lys Gly Gly Arg Ala Lys Asp Cys
1               5


<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Glu Thr Arg Ala Pro Leu
1               5
```